(12) United States Patent
Gautam et al.

(10) Patent No.: US 11,684,338 B2
(45) Date of Patent: Jun. 27, 2023

(54) METHODS AND COMPUTING SYSTEM FOR PROCESSING ULTRASOUND IMAGE TO DETERMINE HEALTH OF SUBDERMAL TISSUE

(71) Applicant: VITRUVIA HOLDINGS INC., Miami Beach, FL (US)

(72) Inventors: Abhinav Gautam, Miami Beach, FL (US); Narendra Kini, Miami Beach, FL (US); Christian Seale, Miami Beach, FL (US); Subhash Kak, Miami Beach, FL (US)

(73) Assignee: VITRUVIA HOLDINGS INC., Miami Beach, FL (US)

( * ) Notice: Subject to any disclaimer, the term of this patent is extended or adjusted under 35 U.S.C. 154(b) by 0 days.

(21) Appl. No.: 17/811,249

(22) Filed: Jul. 7, 2022

(65) Prior Publication Data
US 2022/0338834 A1    Oct. 27, 2022

Related U.S. Application Data

(63) Continuation of application No. PCT/US2021/012708, filed on Jan. 8, 2021.
(Continued)

(51) Int. Cl.
*A61B 8/08* (2006.01)
*G16H 30/40* (2018.01)

(52) U.S. Cl.
CPC .......... *A61B 8/0858* (2013.01); *A61B 8/5223* (2013.01); *G16H 30/40* (2018.01)

(58) Field of Classification Search
CPC ..... A61B 8/0858; A61B 8/5223; A61B 90/00; G16H 30/40; G16H 50/20
See application file for complete search history.

(56) References Cited

U.S. PATENT DOCUMENTS

| 5,776,063 A * | 7/1998 | Dittrich .................. A61B 8/481 |
| | | 600/458 |
| 2002/0186875 A1* | 12/2002 | Burmer .................. G06V 20/69 |
| | | 382/133 |

(Continued)

FOREIGN PATENT DOCUMENTS

| WO | 2014/031760 A1 | 2/2014 |
| WO | 2019/246580 A1 | 12/2019 |

OTHER PUBLICATIONS

Cunningham RJ, Loram ID. 2020 Estimation of absolute states of human skeletal muscle via standard B-mode ultrasound imaging and deep convolutional neural networks. J. R. Soc. Interface 17:20190715. http://dx.doi.org/10.1098/rsif.2019.0715.*

(Continued)

*Primary Examiner* — Bo Joseph Peng
(74) *Attorney, Agent, or Firm* — Medler Ferro Woodhouse & Mills PLLC

(57) ABSTRACT

A computing system and a non-transitory computer-readable medium with instructions for processing ultrasound images are presented. The computing system is configured to: receive an ultrasound image that includes image data representing subdermal tissue; apply a trained neural network to the ultrasound image to generate at least one of: a pliability parameter value which indicates pliability of the subdermal tissue, one or more regions of the ultrasound image that represents damaged tissue, or an indication of presence and/or location of an entrapped nerve.

12 Claims, 29 Drawing Sheets

Related U.S. Application Data

(60) Provisional application No. 62/958,430, filed on Jan. 8, 2020.

(56) References Cited

U.S. PATENT DOCUMENTS

| | | | |
|---|---|---|---|
| 2007/0179367 A1* | 8/2007 | Ruchti | A61B 5/1455 600/316 |
| 2014/0316388 A1* | 10/2014 | Hipsley | A61F 9/00802 606/4 |
| 2015/0323503 A1* | 11/2015 | Openshaw | A61B 5/7275 702/19 |
| 2016/0106347 A1 | 4/2016 | Patwardhan et al. | |
| 2017/0217102 A1* | 8/2017 | Mansi | G16H 50/50 |
| 2017/0281094 A1 | 10/2017 | Ghaboussi et al. | |
| 2018/0000339 A1* | 1/2018 | Hipsley | G16H 20/40 |
| 2020/0261051 A1* | 8/2020 | Yardibi | A61B 34/20 |
| 2021/0216822 A1* | 7/2021 | Paik | G16H 30/40 |
| 2022/0039965 A1* | 2/2022 | Casey | A61F 2/4425 |

OTHER PUBLICATIONS

Hug F, Tucker K, Gennisson JL, Tanter M, Nordez A. Elastography for Muscle Biomechanics: Toward the Estimation of Individual Muscle Force. Exerc Sport Sci Rev. Jul. 2015;43(3):125-33. doi: 10.1249/JES.0000000000000049. PMID: 25906424.*

Azizi A (2017) Designing of Artificial Intelligence Model-Free Controller Based on Output Error to Control Wound Healing Process. Biosens J 6: 147. DOI: 10.4172/2090-4967.1000147.*

L. Hu, L. Li, H. Wang, Z. Bi, X. Zhang and M. Lu, "Quantitative Evaluation of Female Pelvic Floor Muscle Biomechanics Using Ultrasound Elastography," in IEEE Access, vol. 7, pp. 60940-60946, 2019, doi: 10.1109/ACCESS.2019.2909542.*

International Search Report and Written Opinion, International Application No. PCT/US2021/012708, dated Mar. 25, 2021, 11 pages.

Chang et al., "Ultrasound Imaging for the Cutaneous Nerves of the Extremities and Relevant Entrapment Syndromes: From Anatomy to Clinical Implications," J. Clin. Med. 7(457):1-26 (2018).

* cited by examiner

| TEST NAME | RESULT |
|---|---|
| AVG. OVERALL DENSITY | 60.20% |
| W/IN DERMIS, CONNECTIVE TISSUE | 78.83% |
| W/IN MUSCULAR | 50.93% |
| AVG. PRESENCE OF DENSE CLUSTERS | 3.37% |
| W/IN DERMIS, CONNECTIVE TISSUE | 2.96% |
| W/IN MUSCULAR | 3.58% |
| RATIO OF CLUSTERED TO OVERALL | 0.06 |
| W/IN DERMIS, CONNECTIVE TISSUE | 0.04 |
| W/IN MUSCULAR | 0.07 |
| AVG. NO. OF IRREGULARITIES | 18.9 |
| W/IN DERMIS, CONNECTIVE TISSUE | 7.6 |
| W/IN MUSCULAR | 9.5 |

*Irregularities may be calcifications or areas of distress between soft tissue layers*

FIG. 8B

METHODS AND COMPUTING SYSTEM FOR PROCESSING ULTRASOUND IMAGE TO DETERMINE HEALTH OF SUBDERMAL TISSUE

CROSS-REFERENCE TO RELATED APPLICATION(S)

The present application is a continuation of PCT Application No. PCT/US2021/012708 entitled "METHODS AND COMPUTING SYSTEM FOR PROCESSING ULTRASOUND IMAGE TO DETERMINE HEALTH OF SUBDERMAL TISSUE," and filed Jan. 8, 2021, which claims the benefit of U.S. Provisional Application No. 62/958,430, entitled "METHODS AND COMPUTING SYSTEM FOR PROCESSING ULTRASOUND IMAGE TO DETERMINE HEALTH OF CONNECTIVE TISSUE LAYER," and filed Jan. 8, 2020, the entire contents of each of which is incorporated by reference herein.

FIELD OF THE INVENTION

The present invention has application in image processing, machine learning, and sonography.

SUMMARY

The present disclosure relates to a computing system, a method, and instructions on a non-transitory computer-readable medium for processing ultrasound images. The computing system may receive an ultrasound image that includes image data representing subdermal tissue, and apply a trained neural network to the ultrasound image to generate at least one of: a pliability parameter value which indicates pliability of the subdermal tissue, one or more regions of the ultrasound image that represents damaged tissue, or an indication of presence and/or location of an entrapped nerve.

BRIEF DESCRIPTION OF THE DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 7A-7B and 8A-8B depict information which indicates health of a connective tissue layer.

DETAILED DESCRIPTION

Figure 1:
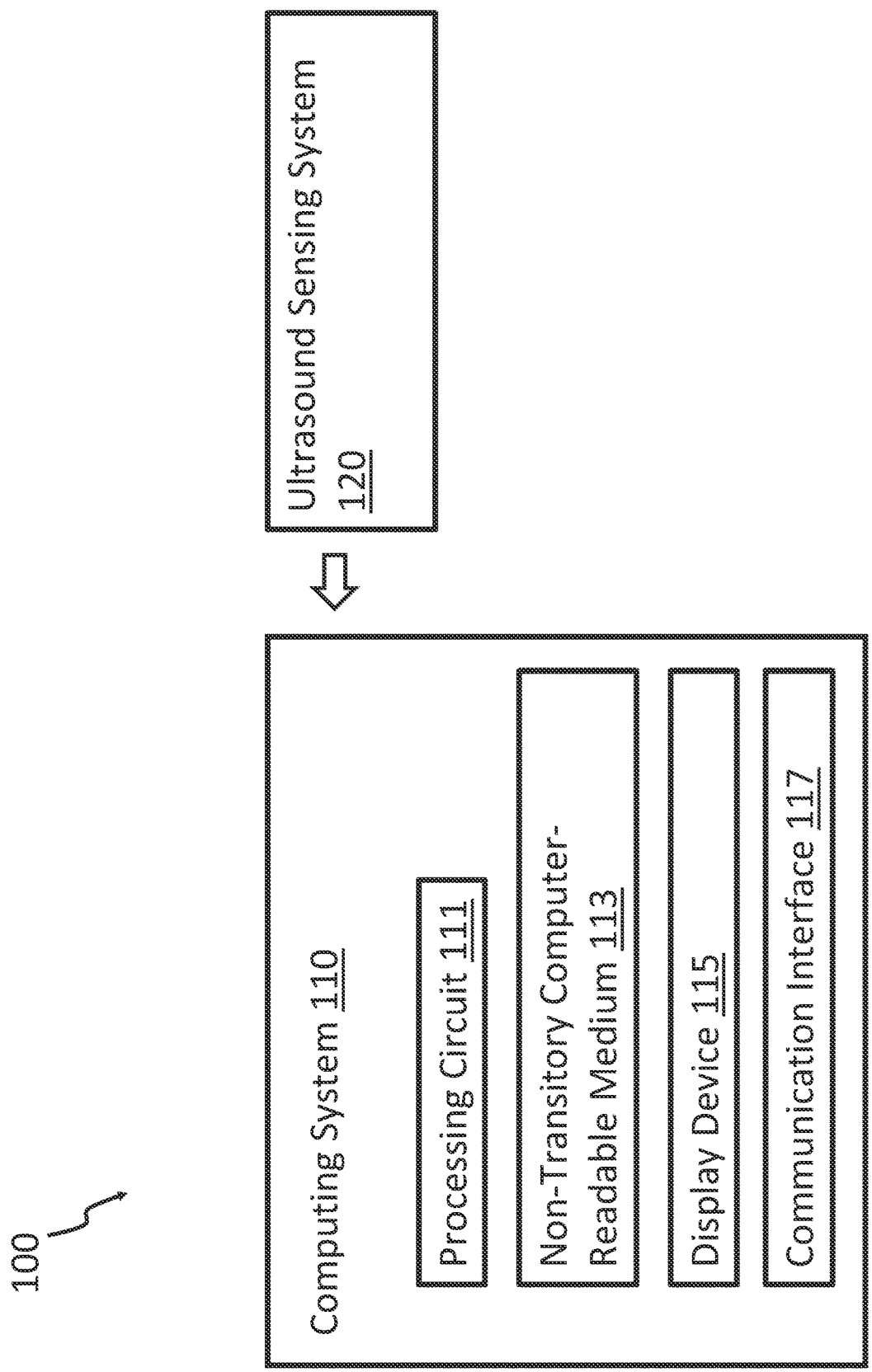
FIG. 1 provides a block diagram of a system for processing ultrasound imaging data to assess health of connective tissue.

The following detailed description is merely exemplary in nature and is not intended to limit the invention or the application and uses of the invention. Furthermore, there is no intention to be bound by any expressed or implied theory presented in the preceding technical field, background, brief summary or the following detailed description. Specific embodiments of the present invention are now described with reference to the figures, wherein like reference numbers indicate identical or functionally similar elements.

One aspect of the embodiments herein relates to a computing system for processing an ultrasound image using a trained neural network (or other form of machine learning) to assess health of connective tissue (or, more generally, mesoderm-derived tissue) captured or otherwise represented by the ultrasound image. The ultrasound image may be derived from performing ultrasound scanning to sense subdermal tissue that is, e.g., within 2-5 cm of the skin surface. In an embodiment, the ultrasound image may represent at least a connective tissue layer within that depth, wherein the connective tissue layer may be located between the skin and muscle. In some instances, the ultrasound image may represent the connective tissue layer as well as underlying layers (e.g., deeper layers), such as a muscle layer and/or a bone layer.

In an embodiment, the computing system may receive an ultrasound image that represents subdermal tissue, and may use a trained neural network to assess overall health of tissue represented by the ultrasound image. The subdermal tissue may include, e.g., a layer of connective tissue. In some cases, the neural network may be used to generate a value or range of values which indicate the health of the tissue represented by the ultrasound image. For instance, the computing system may use the trained neural network to generate a value of a pliability parameter that indicates pliability or mobility of tissue represented by the ultrasound image, wherein the value of the pliability parameter may be an inverse of a value of a stiffness parameter that indicates stiffness of the connective tissue layer. In other words, the pliability parameter may indicate how much mobility or pliability there is in the tissue represented by the ultrasound image, or indicate how little stiffness there is in the tissue. The value of the pliability parameter may be referred to as a pliability parameter value or a pliability score, and may be the inverse of a stiffness parameter value or stiffness score. In a more specific example, the pliability score may indicate tissue fluidity. In such an example, a higher pliability score may indicate that more soft tissue and less hard tissue are found or represented in the ultrasound image, while a lower pliability score may indicate that more hard tissue and less soft tissue are found in or represented in the ultrasound image. Thus, one aspect of the embodiments herein relates to a computing system that is configured to use a trained neural network and an ultrasound image(s) to generate a metric which indicates health, or more specifically pliability, of connective tissue represented in the ultrasound image(s). This metric may be a pliability parameter value (also referred to as a pliability score), which may be used to measure pliability of connective tissue.

In an embodiment, the pliability score may indicate pliability or mobility specifically for a connective tissue layer in the ultrasound image. In that embodiment, the pliability score may indicate, for example, whether a patient may experience a normal level of mobility from that connective tissue layer, or whether the patient may experience stiffness and lack of mobility from that connective tissue layer. For some implementations, the pliability score may indicate or may be affected by a ratio between an amount of damaged connective tissue and an amount of healthy connective tissue in the connective tissue layer. Damaged connective tissue may be identified based on, e.g., tissue density information. In an embodiment, damage to connective tissue may refer to, e.g., calcification (e.g., as a result of scarring), fusion or blockage within the connective tissue layer, or any other type of damage.

In an embodiment, the computing system may use a trained neural network to convert an input ultrasound image, which captures at least connective tissue (e.g., connective tissue, muscle, and bone), into one or more pliability scores. For example, if the ultrasound image includes one image portion representing a connective tissue layer, and includes another image portion representing a muscle tissue layer, then the one or more pliability scores may include a first pliability score which indicates an overall health or mobility of all tissue represented in the ultrasound image (e.g., a combination that includes connective tissue, muscle tissue, but not bone), a second pliability score that indicates health or mobility specifically of connective tissue in the ultrasound image, and a third pliability score that indicates health or mobility specifically of any muscle tissue captured in the ultrasound image, or of some other tissue or body part represented in the ultrasound image.

In an embodiment, the neural network may be trained and used by the same computing system, or may be trained by a first computing system, and then used by another computing system. If the neural network is used to generate a pliability score based on an ultrasound image, the first computing system may train the neural network by providing training images, or more specifically ultrasound images, and by providing pliability scores associated with the training images. In some instances, the training images may include a first set of ultrasound images that represent connective tissue with a relatively low level of mobility (and a relatively high level of stiffness), and include a second set of ultrasound images that represent connective tissue with a relatively high level of mobility (and a relatively low level of stiffness). For example, the first set of ultrasound images may be captured from patients who are experiencing stiffness or who have been diagnosed as having damaged connective tissue, and the second set of ultrasound images may be captured from the same patients after receiving treatment to successfully rehabilitate their connective tissue. In some implementations, the pliability scores used for training the neural network may be provided by a clinician or other doctor treating the patients. In some instances, the pliability scores used for training may have been determined based on analyzing the ultrasound images. For example, the pliability scores may be determined (e.g., manually) based on how much calcification or other scarring in the connective tissue is indicated by the ultrasound images. In some instances, the pliability scores used for training may have been determined without relying on the ultrasound images. For example, they may be determined based on information reported by a patient, such as a level of pliability or stiffness in connective tissue, pain being experienced by the patient in or around connective tissue, or the patient experiencing a lack of mobility or pliability in the connective tissue. In some instances, the pliability scores used for training may have been determined based on a combination of the examples discussed above.

In an embodiment, the neural network may be a convolutional neural network, a corner neural network, or some other neural network. For example, the neural network may be a convolutional neural network having a sequence of convolutional layers. The sequence of convolutional layers may include a first convolutional layer that is configured to apply a convolutional filter on an input ultrasound image to generate an activation map, and include additional convolutional filters that are configured to apply respective convolutional filters on respective activation maps or other outputs of previous convolutional filters in the sequence. In some implementations, the sequence of convolutional layers may each include a respective activation layer and/or a maxpooling layer. The activation layer may, e.g., apply an activation function (e.g., a rectified linear unit (ReLU) function) to an output of a convolutional filter in the convolutional layer. The maxpooling layer may be configured to, e.g., consolidate multiple values from an output of the activation layer into a single value. In some implementations, the training of the neural network may involve the first computing system adjusting weights or other parameter values of the convolutional filters or other components of the convolutional layers, so as to cause the sequence of convolutional layers to convert the training images to output values which are equal to the pliability scores used for training, or which have a low amount of deviation from the pliability scores used for training.

In an embodiment, the computing system may use a trained neural network to identify, from an ultrasound image, one or more regions in the ultrasound image that represents one or more respective locations at which there is an entrapped subcutaneous nerve(s) (e.g., a subcutaneous nerve associated with a neurofascial abnormality). The trained neural network may be the same neural network configured to generate a pliability score(s) based on the ultrasound image, or may be a different neural network. The neural network may have been trained (e.g., by the computing system) based on an ultrasound image for a body part of a patient, and based on information that indicates whether the patient is experiencing pain in that body part, and/or information that indicates a location of the pain. In some instances, the ultrasound image may represent a connective tissue layer, a muscle layer covered by or otherwise adjacent to the connective tissue layer, and a bone adjacent to the muscle layer. In some implementations, training the neural network may involve inferring a location at which there is likely an entrapped nerve. The inference may be based on, e.g., an overlap between regions in the ultrasound image that represent damaged tissue or blockage of a fluid channel, and nerve location information that defines a path of a nerve (e.g., ulnar nerve) going through that body part. If, for instance, the nerve location information is overlaid on the ultrasound image, the location of an entrapped nerve may be where the known path of the nerve runs through one of the locations at which there is tissue damage or channel blockage. This determination may be used to train the neural network to identify areas of interest in which there is likely an entrapped nerve. In some implementations, the trained neural network may be configured to output a location (e.g., a pixel location) in the ultrasound image at which there is a sufficient likelihood of an entrapped nerve.

In an embodiment, the computing system may use a trained neural network to identify one or more regions of an ultrasound image that represent damaged connective tissue within a connective tissue layer, or more generally to identify one or more regions of interest. The neural network may be the same neural network used to generate a pliability score and/or to identify an entrapped nerve, or may be a different neural network. In this embodiment, the neural network may have been trained (e.g., by the computing system) to recognize features such as regions within the ultrasound image that represent a cluster of high density within the connective tissue layer, and/or a region that represents irregular structure in the connective tissue layer. The irregular structure may include, e.g., a cluster having a non-symmetric shape, or a location at which the connective tissue layer has a disorganized structure, such as a non-laminar structure. The above features may indicate calcification, adhesion, scarring, or other damage in a connective tissue layer.

In some cases, the neural network may be trained to recognize non-laminar structure in the connective tissue layer. More particularly, healthy connective tissue may tend to exhibit laminar structure. The ultrasound images for the healthy connective tissue may show distinct continuous lines that demarcate clear borders between various layers or structures within the connective tissue layer, such as a border between a fluid channel and surrounding tissue of the connective tissue layer. The neural network may be trained to recognize a laminar structure (e.g., by recognizing lower-level features such as broken or otherwise non-contiguous lines), and to recognize when a laminar structure is not present in a connective tissue layer. In some cases, the lack of a laminar structure in the connective tissue layer may represent, e.g., of the fluid channel. Because the fluid channel may bring nutrients and eliminate debris for the connective tissue layer, blockage of the fluid channel may be correlated with damage to the connective tissue layer. More particularly, blockage of the fluid channel may lead to blockages of the connective tissue, lack of mobility, and stiffness.

In some cases, the computing system may perform image segmentation so as to identify the one or more regions of interest, or more specifically one or more regions that represent connective tissue which is likely to be damaged. For example, the computing system may use the trained neural network to generate, from an ultrasound image, one or more locations (e.g., pixel locations) at which there is an image feature that corresponds to damaged connective tissue. In some instances, the trained neural network may further generate, from the ultrasound image, a value(s) of a size or dimension of a respective region (e.g., a bounding box or bounding circle) surrounding each of the one or more locations. In some cases, the size or dimensions of the region may correspond to a size or dimensions of an image feature at a location enclosed by the region. In other words, the trained neural network may be configured to recognize an image feature which corresponds to damaged connective tissue in an ultrasound image, and may be configured to identify a region which approximates an outline or contour of the image feature.

In an embodiment, the computing system may use a trained neural network to output tissue density information that indicates density of a connective tissue layer represented by the ultrasound image. In other embodiments, the tissue density information may be determined by some other component (e.g., some other software module). The tissue density information may be based on, e.g., image intensity information, such as respective intensities of the pixels of the ultrasound image. For example, a higher intensity value for a pixel may indicate higher density at a location corresponding to the pixel, and a lower intensity value for the pixel may indicate lower density at the location.

In some cases, the tissue density information may indicate overall density of the connective tissue layer, which may be expressed as, e.g., a percentage of dense tissue to fluid tissue. In some cases, the tissue density may indicate how much of the connective tissue layer is occupied by one or more high-density clusters. Each of the one or more high-density clusters may be a cluster that has a density higher than that of a surrounding region, and which exceeds a defined threshold.

In some instances, higher density at a particular location of the connective tissue layer may reflect dehydration, inflammation, and even stress at that location. In some instances, higher density at a particular location of the connective tissue layer may reflect calcification, which may increase an average amount of tissue density and decrease an average amount of tissue fluidity around that location. The calcification may be, e.g., a sign of scarring at that location, and thus may indicate damaged connective tissue at that location. Thus, each of the above factors may indicate potential connective tissue damage and/or health of the connective tissue layer.

In some instances, the computing system may use a trained neural network to classify the connective tissue layer as being normal/healthy versus being abnormal/stiff. Such a classification may be made based on, e.g., the tissue density information, such as tissue density values. For instance, the neural network may be trained to output such a classification based on an input ultrasound image. In an embodiment, the neural network may have been trained based on ultrasound images of patients, and symptomology information for the patients. The symptomology information for the patients may involve, e.g., whether the patients reported experiencing pain, stiffness, and/or lack of mobility in an area being scanned by ultrasound. In some implementations, the neural network may be trained to associate tissue density information from the ultrasound images of those patients with their symptomology information. The neural network may be trained with such information so as to be able to distinguish between tissue density information (e.g., density values) that are considered to belong to normal/healthy connective tissue, versus tissue density information that are considered to belong to abnormal/stiff connective tissue. In other words, the neural network may be trained to establish which density values are normal/healthy for a population of patients, and which density values are abnormal/indicative of low mobility for the population of patients.

In an embodiment, the trained neural network may be trained to remove (e.g., strip out) image information which represents any image portion that represents bone underlying the connective tissue. For instance, the trained neural network may be configured to convert an input ultrasound image to an updated ultrasound image that segments out (e.g., extracts) the connective tissue layer. In such an embodiment, the neural network may be trained to distinguish between image data that is attributable to the connective tissue layer and/or muscle layer versus image data that is attributable to the bone, and may be configured to generate an updated ultrasound image that removes the effect of the image data that is attributable to the bone. In some instances, image data of the updated ultrasound image may represent tissue at only a certain range of depths, such as 2-5 cm. The health of the connective tissue layer may be determined using the updated ultrasound image that represents only the connective tissue layer, or only the connective tissue layer and the muscle layer.

In an embodiment, if an ultrasound image represents muscle tissue, the above techniques used for assessing health of connective tissue may also be used to assess health of muscle tissue. For example, a neural network may be trained to recognize whether the muscle exhibits organized structure, or whether the muscle lacks organized structure, and to assess health of the muscle tissue based on those features.

The above embodiments may be implemented separately, or may be combined. For example, the combination may involve the use of one or more neural networks to extract an image portion from the ultrasound image that represents a connective tissue layer (e.g., by filtering out image data that represents the bone), to determine tissue density information (e.g., an overall density) of the connective tissue layer, to recognize various features in the extracted image portion, including presence of non-contiguous lines across the connective tissue layer, presence of fusion or calcification in the connective tissue layer, presence of a cluster having a depth-to-width ratio that exceeds a defined threshold (e.g., a threshold of 1), and to recognize a region of the extracted image portion that represents a location at which there is an entrapped nerve in the connective tissue layer or under the connective tissue layer. Such a combination may use a single neural network, or may involve multiple neural networks. The clusters or regions that are discussed above may be marked as areas of interest in the ultrasound image.

FIG. 1 depicts a system 100 for assessing the health of tissue captured or otherwise represented by an ultrasound image, or more specifically an ultrasound image which represents at least connective tissue. As illustrated in the figure, the system 100 includes a computing system 110 and an ultrasound sensing system 120. In an embodiment, the ultrasound sensing system 120 may include a scanner (e.g., Clarius ultrasound scanner) that is configured to emit ultrasound waves at a part of a patient's body and to generate measurement data which describe reflection of the ultrasound waves. For instance, the ultrasound scanning system 120 may be configured to operate at frequency of about 4 Hz to 100 Hz, and may be configured to sense features that are within 10 cm (e.g., within 2.5 cm) from skin surface, wherein this depth range may correspond to musculoskeletal and/or nerve features (as opposed to internal organs). In some cases, the ultrasound sensing system 120 may be configured to generate an ultrasound image or ultrasound images based on the measurement data, and communicate the ultrasound image or images to the computing system 110. In some cases, the ultrasound images may be ultrasound scan frames that are part of a ultrasound video from a video feed, and each ultrasound image may be an individual frame of the video feed. In some cases, the ultrasound scanning system 120 may communicate the measurement data directly to the computing system 110, which may be configured to generate the ultrasound image or images based on the measurement data.

In an embodiment, the ultrasound scanning system 120 may be configured to generate measurement data for mesoderm-derived tissue, which may refer to tissue that comes from the mesoderm, one of the three germinal layers present in embryonic development. Mesoderm-derived tissue may include one or more of connective tissue, muscle, fat, bone, nerve, tendon, and ligament. In an embodiment, the ultrasound image generated based on the ultrasound scanning system may represent subepidermal tissue, including connective tissue. The connective tissue may refer to tissue that joins or is found between other tissues in the body. Connective tissue includes connective tissue proper, and special connective tissue. In one example, connective tissue may be found in structures such as tendons and ligaments, and may be characterized by collagen fibers arranged in an orderly parallel fashion.

As depicted in FIG. 1, the computing system 110 may include at least one processing circuit 111, a non-transitory computer-readable medium 113, a display device 115, and a communication interface 117. In some implementations, the computing system 110 may be or may include a desktop computer, a server, a laptop computer, a tablet computer, a mobile device (e.g., phone), or some other computing system 110. The processing circuit 111 may include, e.g., one or more microprocessors or processing cores, an application-specific integrated circuit (ASIC), field programmable gate array (FPGA), or any other processing circuit. The non-transitory computer-readable medium 113 may include a hard disk drive (HDD), a solid state drive (SSD) or other solid state memory, or any other non-transitory computer-readable medium. The display device 115 may be a separate component from the processing circuit 111 and non-transitory computer-readable medium 113, such as when the computing system 110 is a desktop computer, or these components may be integrated to form a single device, such as when the computing system 110 is a laptop computer or tablet computer. In an embodiment, communication interface 117 may be a circuit or other component, such as a universal serial bus (USB) or Ethernet interface, that is configured to communicate with the ultrasound sensing system 120. For instance, the computing system 110 may be configured to receive ultrasound images from the ultrasound sensing system 120 via the communication interface 117.

Figure 2:
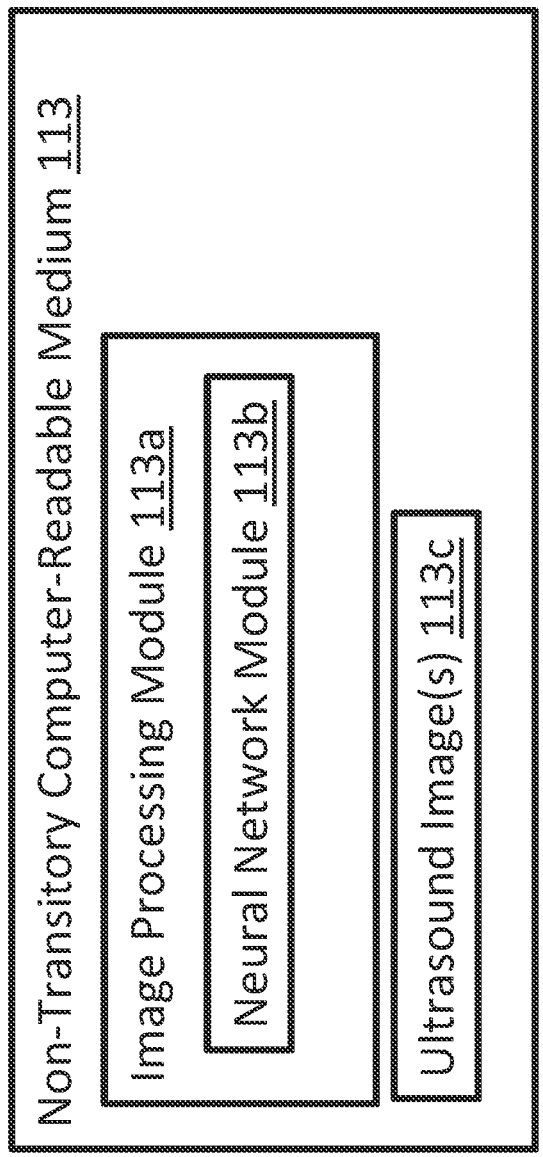
FIG. 2 provides a block diagram of an image processing module configured to process an ultrasound image with a trained neural network.

In an embodiment, as depicted in FIG. 2, the non-transitory computer-readable medium 113 may store ultrasound images 113c, and may include an image processing module 113a. The image processing module 113a may include instructions (e.g., a software library) that, when executed by the processing circuit 111, causes the processing circuit 111 to process the ultrasound images 113c. In some implementations, the image processing module 113a, or more generally, the computing system 110, may be configured to assess health of connective tissue as part of the ScarMap® software package or system.

In an embodiment, the image processing module 113a may include a neural network, or more specifically a neural network module 113b. The neural network module 113b may include parameter values for a trained neural network, such as weights in various layers of the neural network. If the neural network is a convolutional neural network, the weights may belong to convolutional filters in various convolutional layers of the convolutional neural network. The neural network module 113b may further include instructions that, when executed by the processing circuit 111, causes the processing circuit 111 to apply the trained neural network to the ultrasound images 113c to determine health of tissue associated with the ultrasound images 113c.

Figure 3A:
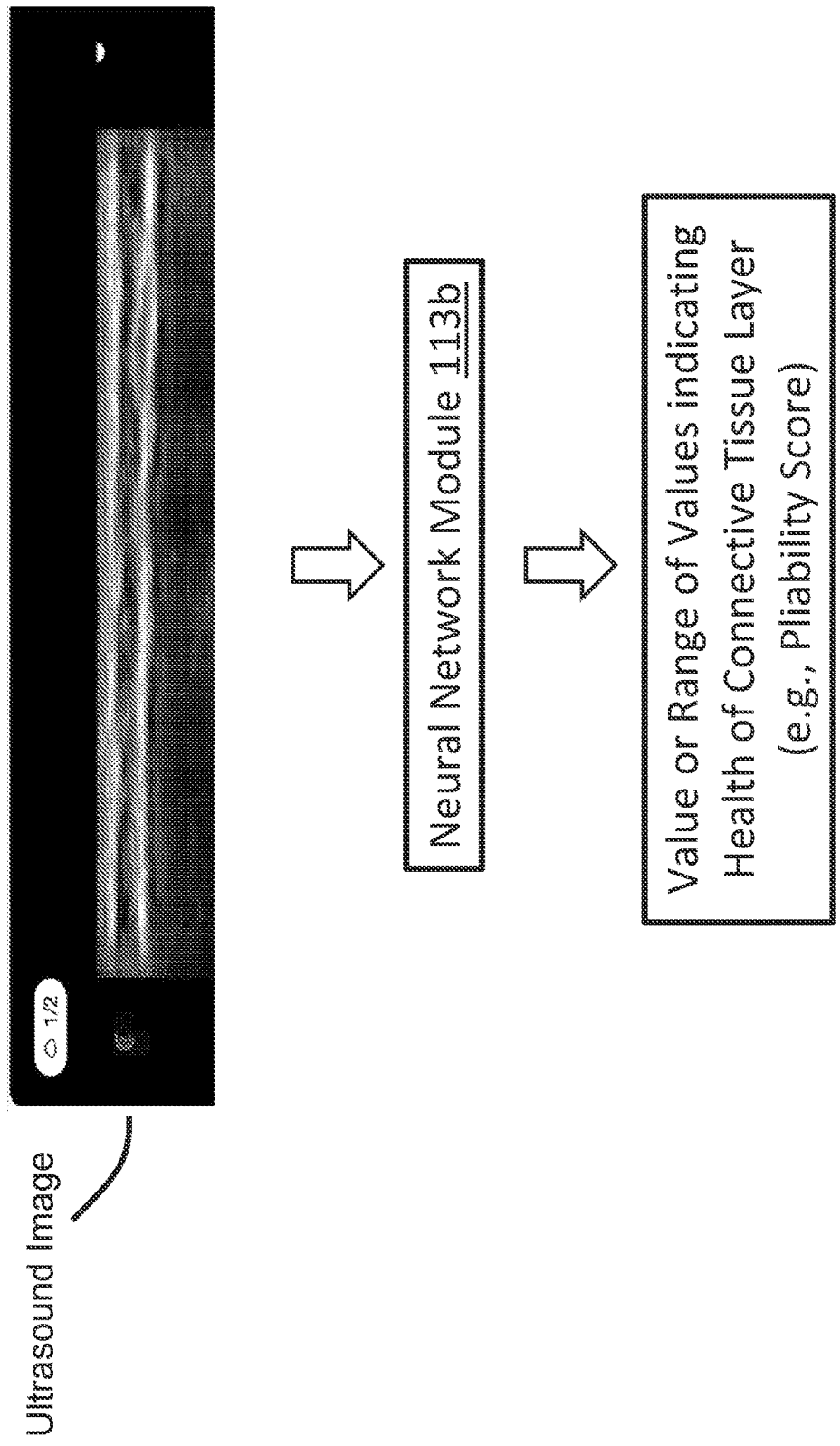
FIG. 3A illustrates a trained neural network that processes an ultrasound image to output a value or range of values which indicate health of a connective tissue layer.

As discussed in more detail below, the trained neural network of the neural network module 113b may be configured to output, based on an ultrasound image that includes a connective tissue layer, one or more values which indicate health of the connective tissue layer, output information which identifies regions of the ultrasound image that represents damaged connective tissue, and/or output information which identifies regions of the ultrasound image that represent a location at which there is an entrapped nerve(s) in the connective tissue layer. For example, FIG. 3A illustrates an embodiment in which the trained neural network of the neural network module 113b is configured to output, based on an ultrasound image that includes a connective tissue layer, a value or range of values indicating health of the connective tissue layer. In some instances, the value or range of values may be a pliability parameter value, also referred to as a pliability score, which indicates mobility (or, inversely, stiffness) of the connective tissue layer. As discussed below in more detail, the pliability score may be, e.g., a score that is based on or affected by a ratio between how much healthy connective tissue is present in the connective tissue layer and how much damaged connective tissue is present in the connective tissue layer. In some instances, the pliability score may be normalized to a particular scale, such as a scale which has a minimum value of zero and a maximum value of 100. Such a normalization may simplify interpretation of the pliability score, by facilitating an understanding of whether the pliability score for a particular patient is within some average or median range for a patient population, or whether the pliability score for that particular patient is abnormally high or abnormally low. In some instances, the computing system 110, or more specifically the neural network module 113b, may output the pliability score based on an ultrasound image of a patient's connective tissue, and the pliability score may be used to determine whether the patient needs rehabilitation or other treatment for a particular connective tissue layer in the patient's body, or to determine how to administer that rehabilitation or treatment.

In an embodiment, the neural network used by the neural network module 113b may have also been trained by the computing system 110, or may be trained by a different computing system. The training may be performed with, e.g., training ultrasound images that represent healthy connective tissue that have a relatively high level of pliability or mobility, and training ultrasound images that represent damaged connective tissue that have a relatively low level of pliability or mobility. The training ultrasound images may be associated with training pliability scores, which may act as a metric that measures health of the connective tissue. In some scenarios, the training pliability scores may be determined by clinicians, based on the training ultrasound images, and/or based on symptology of patients from whom the training ultrasound images are captured. The training of the neural network may involve adjusting the weights or other parameter values of the neural network so as to cause the neural network to compute, based on the training ultrasound images, output values which are the same or substantially similar to the training pliability scores. Training of neural networks is discussed in more detail below with respect to FIGS. 10 through 14.

In an embodiment, the neural network may be configured to output multiple pliability scores based on a single ultrasound image. The pliability scores may be associated with different portions of the ultrasound image, or different regions of the body captured by the ultrasound image. For example, FIG. 3F depicts an implementation in which the neural network module 113b may include or may be configured to access a trained neural network that is configured to process an ultrasound image which represents at least connective tissue and adjacent muscle tissue, or more specifically a connective tissue layer and a muscle tissue layer. The trained neural network may be configured to output, based on the ultrasound image, a first pliability score that represents overall pliability or mobility for all tissue represented in an entirety of the ultrasound image, a second pliability score that indicates pliability or mobility specifically for the connective tissue in the ultrasound image, and a third pliability score that indicates pliability or mobility specifically for the muscle tissue in the ultrasound image. The first pliability score may more specifically be based on a combination of connective tissue and muscle tissue in the entirety of the ultrasound image, and may in some cases ignore or be unaffected by any bone which appears in the ultrasound image. As discussed below in more detail, training the neural network in this embodiment may involve providing training ultrasound images which are each associated with a respective set of three training pliability scores. The set of three training pliability scores may include a first training pliability score that indicates pliability or mobility of all tissue in an entirety of the respective training ultrasound image, a second training pliability score that indicates pliability or mobility specifically of connective tissue in the training ultrasound image, and a third training pliability score that indicates pliability or mobility specifically of muscle tissue in the training ultrasound image.

Figure 3B:
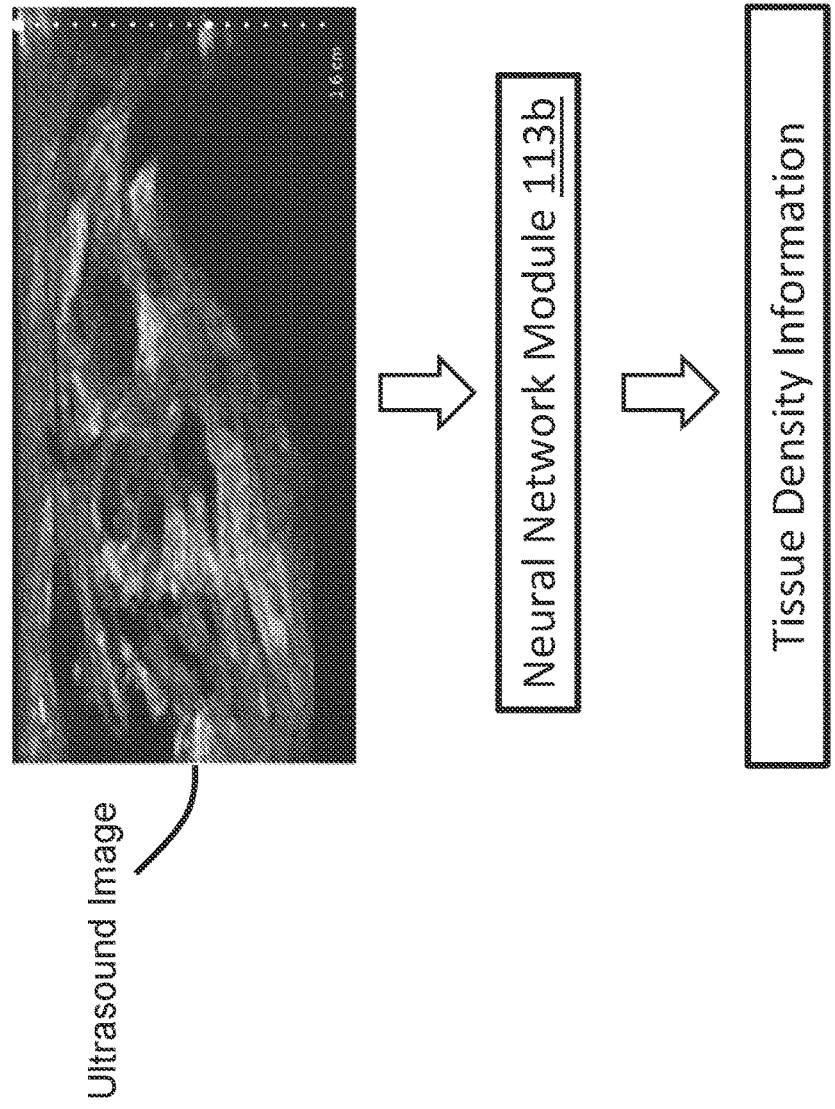
FIG. 3B illustrates a trained neural network that processes an ultrasound image to output tissue density information.

FIG. 3B depicts an example in which the trained neural network of the neural network module 113b is configured to output, based on the ultrasound image(s), tissue density information for the connective tissue layer. The tissue density information may indicate how much of the connective tissue layer is composed of material other than fluid (e.g., other than water), locations in the connective tissue layer at which there are clusters of material having a density which exceeds a defined threshold, respective sizes of the clusters, or any other tissue density information. In some instances, a high-density cluster at a particular location may be indicative of calcification at that location. The calcification may be a sign of scarring, and thus may indicate tissue damage in the connective tissue layer. Thus, the tissue density information may indicate or be used to determine health of the connective tissue layer.

Figure 3C:
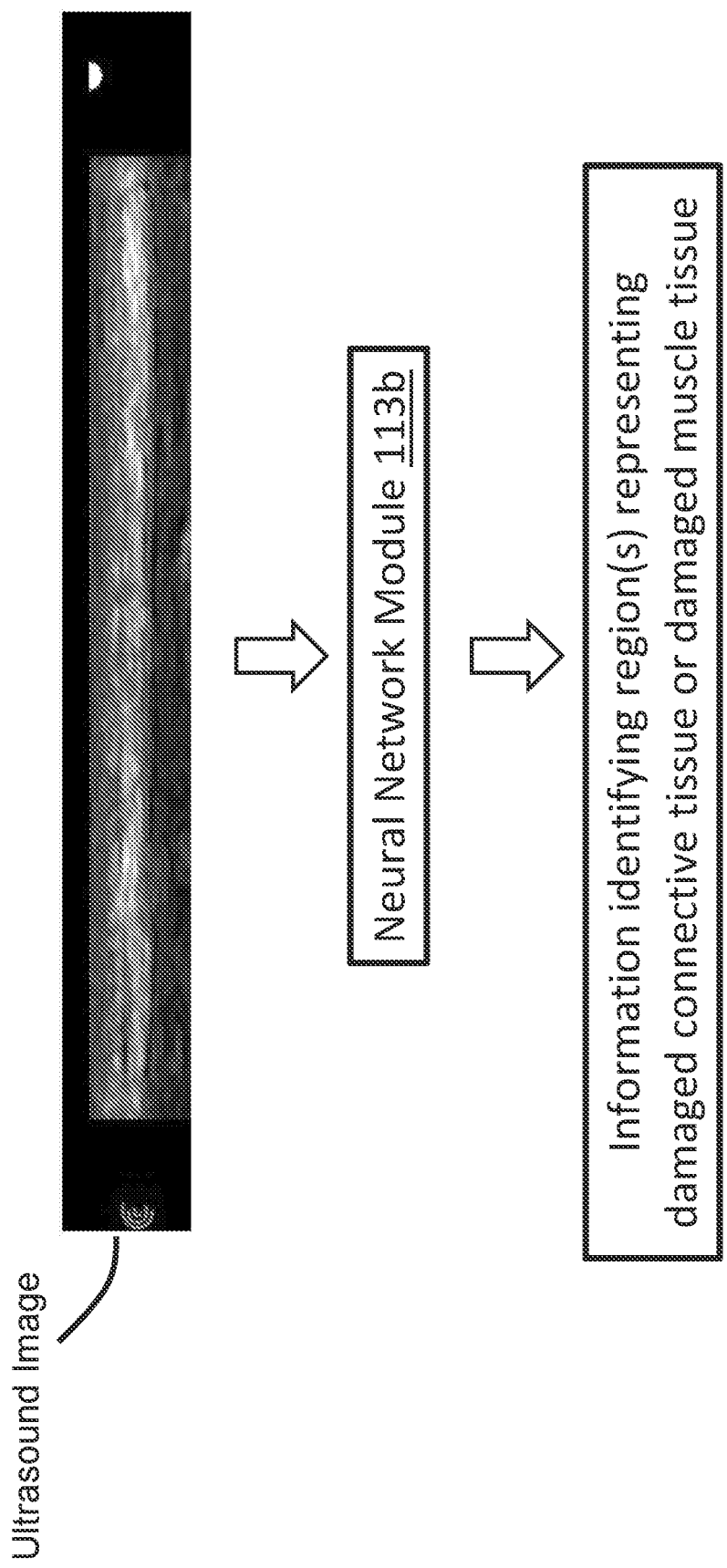
FIG. 3C illustrates a trained neural network that processes an ultrasound image to output information which identifies one or more regions in the image that represent damaged connective tissue.

FIG. 3C provides an example in which the trained neural network of the neural network module 113b is configured to output, based on an ultrasound image representing body tissue, information identifying one or more regions of interest. The regions of interest may more specifically be regions showing signs of damaged tissue, or more specifically damaged connective tissue or damaged muscle tissue. In some cases, the neural network may have been trained to recognize a region as having damaged connective tissue based on density of the region, based on a shape of a cluster at the region (wherein the cluster has a density higher and distinct from that of a surrounding region), how symmetric is the shape of the cluster, a size of the cluster, and/or any other feature of the connective tissue layer.

In an embodiment, the neural network module 113b of FIG. 3C may be configured to perform image segmentation, which may involve identifying a location for a particular region of interest and a boundary for that region. For instance, if the region of interest corresponds to a particular image feature in the ultrasound image, such as a group of pixels representing a high density cluster in the connective tissue represented in the image, the trained neural network of the module 113b may be configured to output a location of the image feature, and to identify boundaries of a region (e.g., a bounding circle) that surrounds the location and has a size similar to that of the image feature. The region may thus indicate an approximate set of locations in the connective tissue in which there is a likelihood or sign of damage to the connective tissue.

Figure 3D:
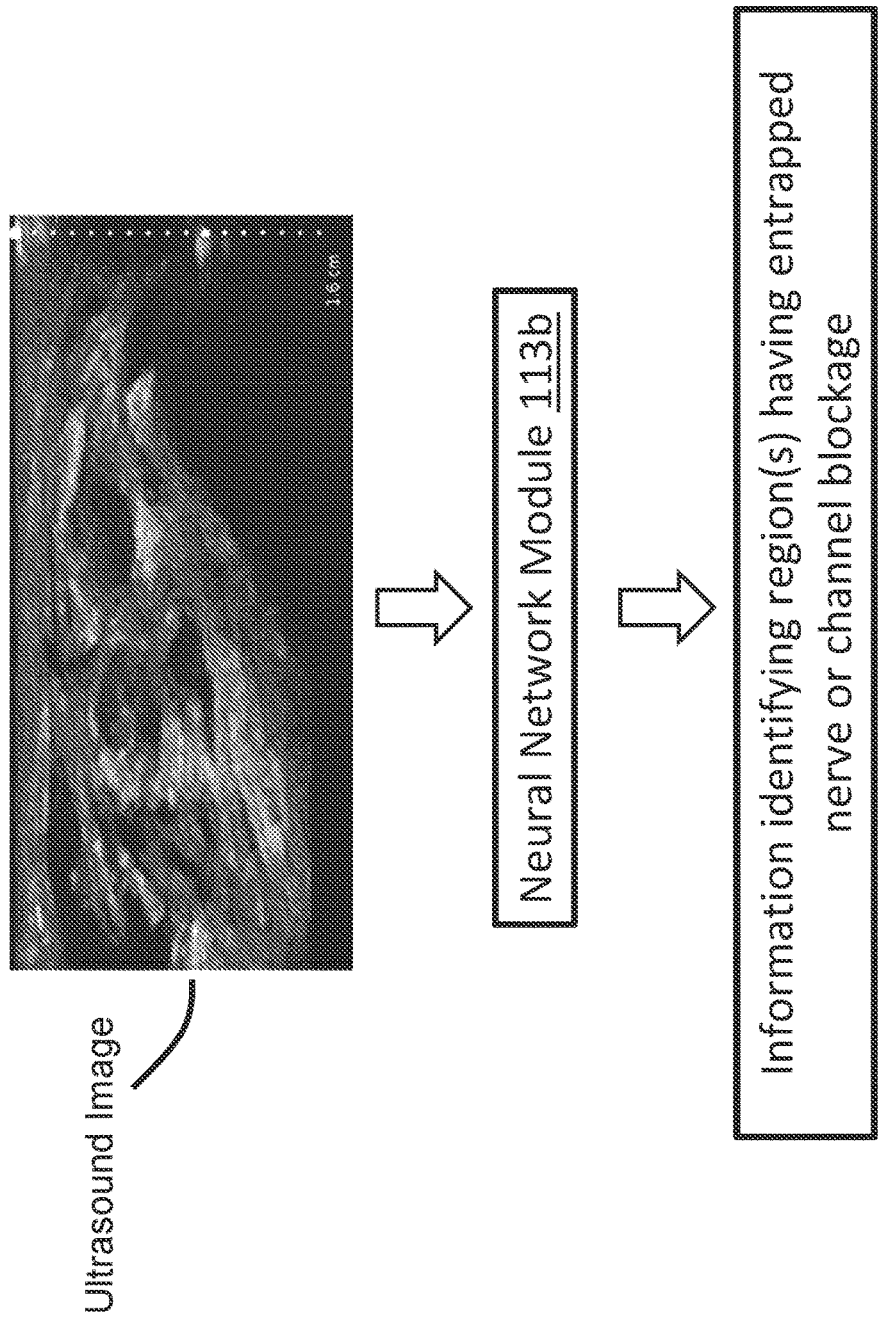
FIG. 3D illustrates a trained neural network that processes an ultrasound image to output information which identifies one or more regions having an entrapped nerve or blockage of a channel in the connective tissue.

FIG. 3D depicts an embodiment in which the trained neural network of the neural network module 113b is configured to output, based on an ultrasound image that includes at least a connective tissue layer, one or more regions of the ultrasound image (e.g., a group of pixels) that represent one or more respective locations of the connective tissue layer at which there is likely an entrapped nerve. As discussed below, the neural network in this embodiment may have been trained with ultrasound images of patients who were experiencing pain. The neural network may further have been trained with information indicating location of an entrapped nerve, wherein the information may have been determined based on location of the pain (which may have been indicated by the patient) and on known information indicating a path of a nerve within the connective tissue layer of the patient.

Figure 3E:
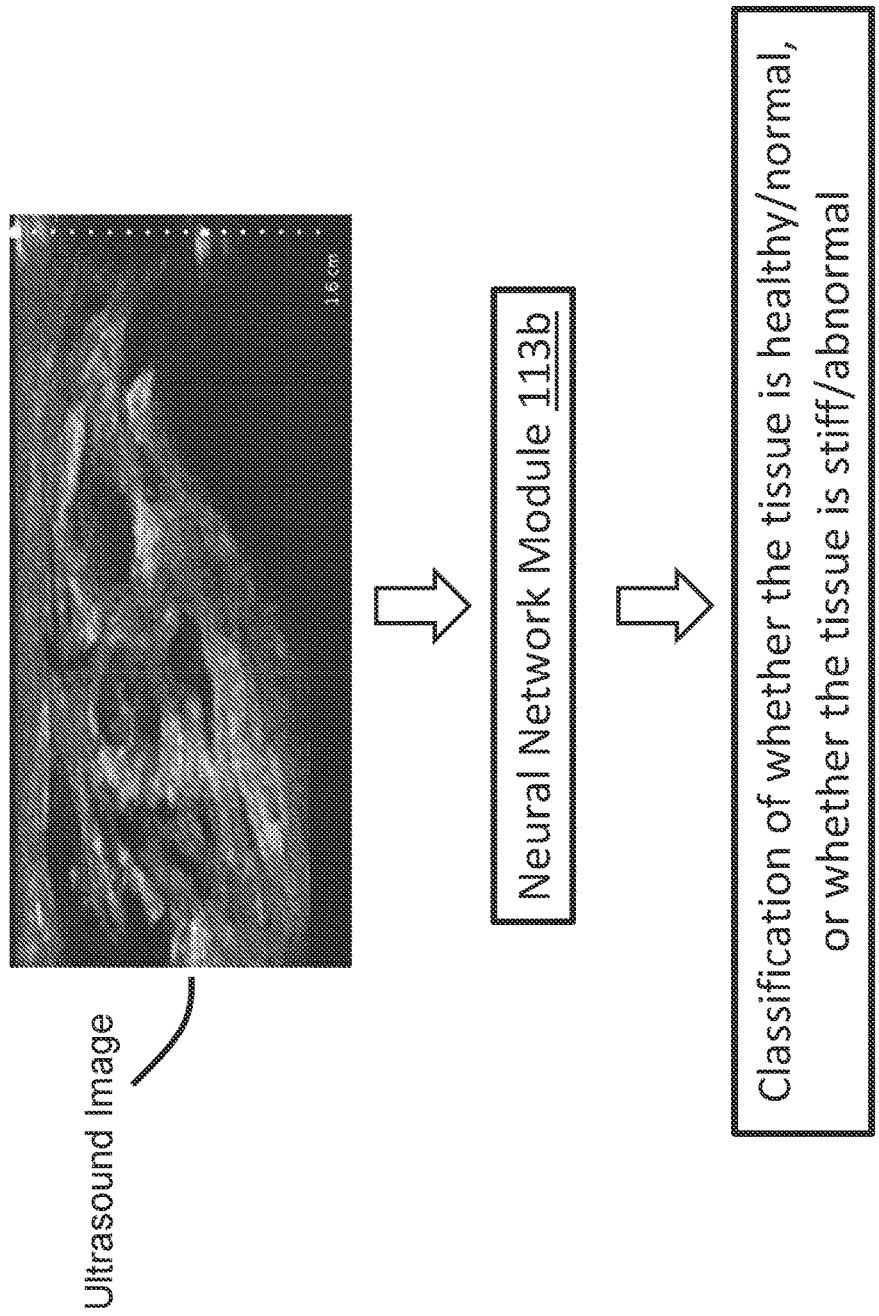
FIG. 3E illustrates a trained neural network that processes an ultrasound image to output a classification of whether connective tissue is normal/healthy, or whether the connective tissue is abnormal/stiff.
Figure 3F:
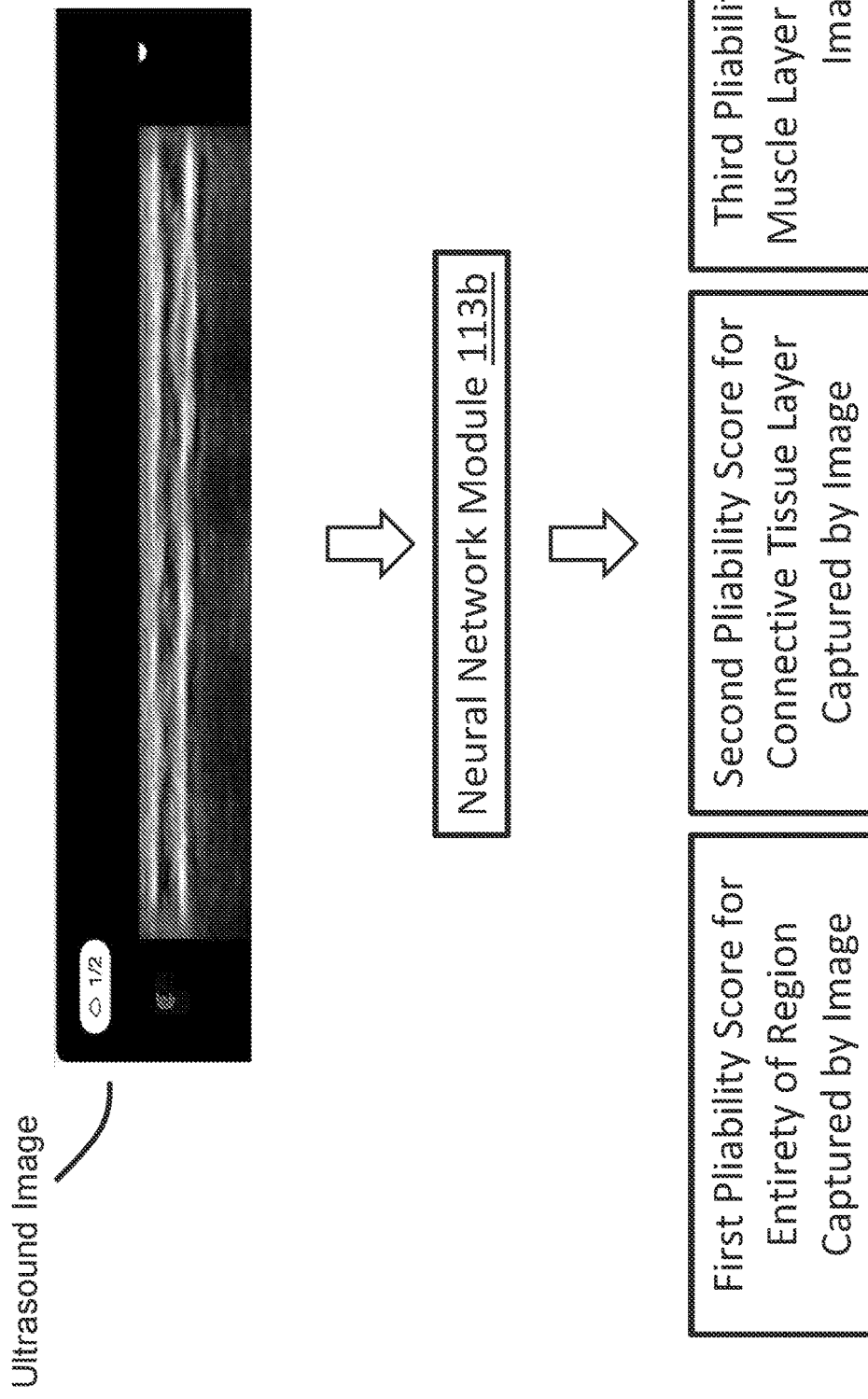
FIG. 3F illustrates a trained neural network that processes an ultrasound image to output multiple pliability scores based on the ultrasound image, according to an embodiment hereof.

FIG. 3E illustrates an embodiment in which the trained neural network of the neural network module 113b is configured to output, based on an ultrasound image that includes connective tissue layer, a classification of whether the tissue is healthy/normal versus whether the connective tissue is abnormal/stiff. In some cases, the neural network may output such a classification based on tissue density information, such as density values for the connective tissue layer. As stated above, the neural network in this example may in some instances have been trained based on ultrasound images of patients and their symptomology. For instance, the symptomology may relate to information from the patients for whether they are experiencing stiffness or low level of mobility. The connective tissue for patients who reported no pain/stiffness/low mobility in a body part from which the ultrasound image is generated may be considered to have a classification of healthy/normal, and the connective tissue of patients who reported sufficient pain/stiffness/low mobility in the body part may be considered to have a classification of abnormal or stiff. In some cases, the neural network may be trained further based on density values of the connective tissue, which may be an additional or alternative input to the neural network. As stated above, training the neural network in this manner may enable the neural network to establish or define which density values are normal, and which density values are abnormal.

Figure 3G:
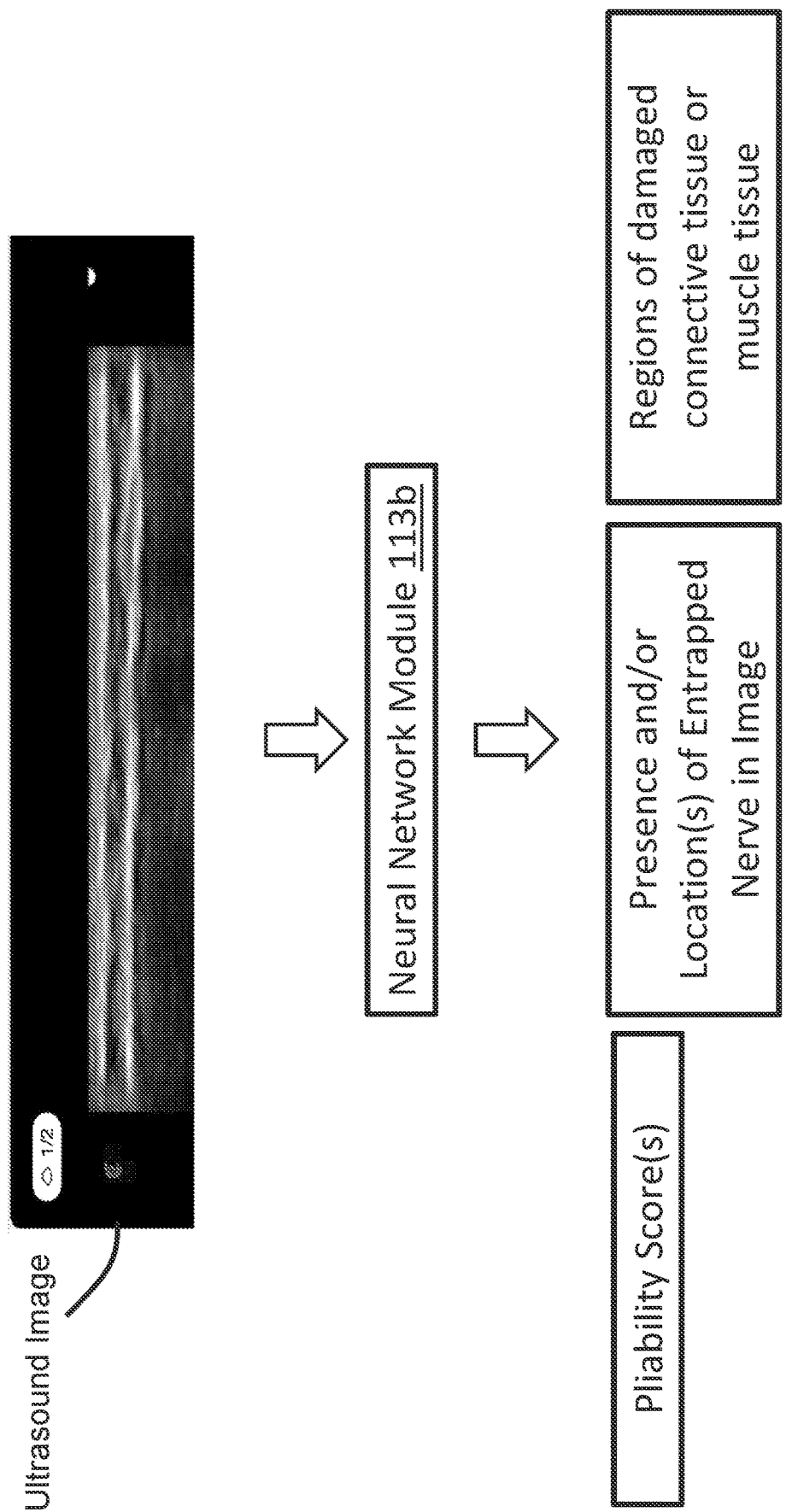
FIG. 3G illustrates a trained neural network that processes an ultrasound image to output multiple types of information, according to an embodiment hereof.

In an embodiment, the trained neural network of the neural network module 113b may be configured to output multiple types of information, such as a combination of the types of information discussed above with respect to FIGS. 3A-3F. For example, FIG. 3G illustrates an example in which the neural network module 113b may be configured to apply an ultrasound image to a trained neural network which is configured to output, based on the ultrasound image, one or more of the pliability scores discussed above with respect to FIGS. 3A and 3F, to output information that identifies presence and/or location of an entrapped nerve as discussed above with respect to FIG. 3D, and to output information that identifies regions of interest discussed above with respect to FIG. 3C, such as regions which include a sign of damaged connective tissue or damaged muscle tissue. As discussed below in more detail, the neural network in this embodiment may be trained with training ultrasound images which are each associated with a respective set of training output information assigned to the training ultrasound image. The set of output information may include one or more training pliability scores, training information which indicates presence and/or location of an entrapped nerve in the training ultrasound image, and training information which indicates one or more regions in the training ultrasound image that represent damaged tissue, such as damaged connective tissue or damaged muscle tissue.

Figure 3H:
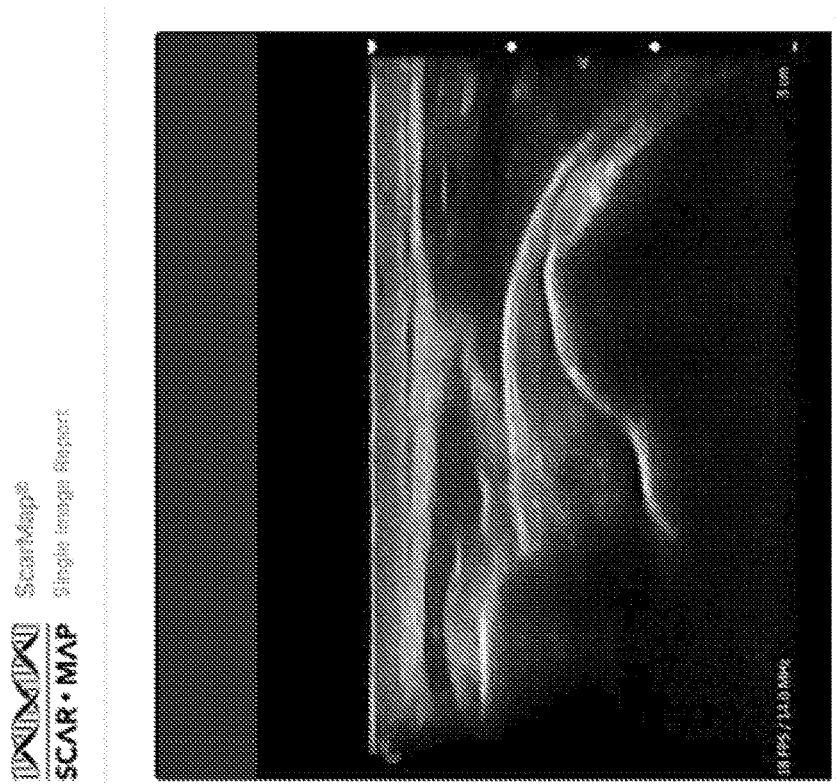
FIGS. 3H and 3I illustrate pliability scores which are generated based on various ultrasound images, according to an embodiment hereof.
Figure 3H:
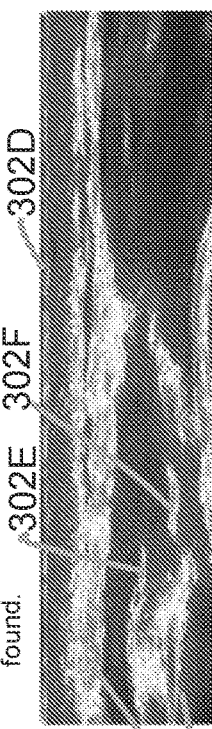
Figure 3H:
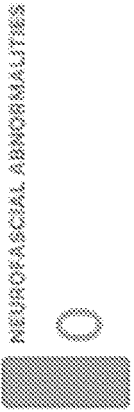
Figure 3I:
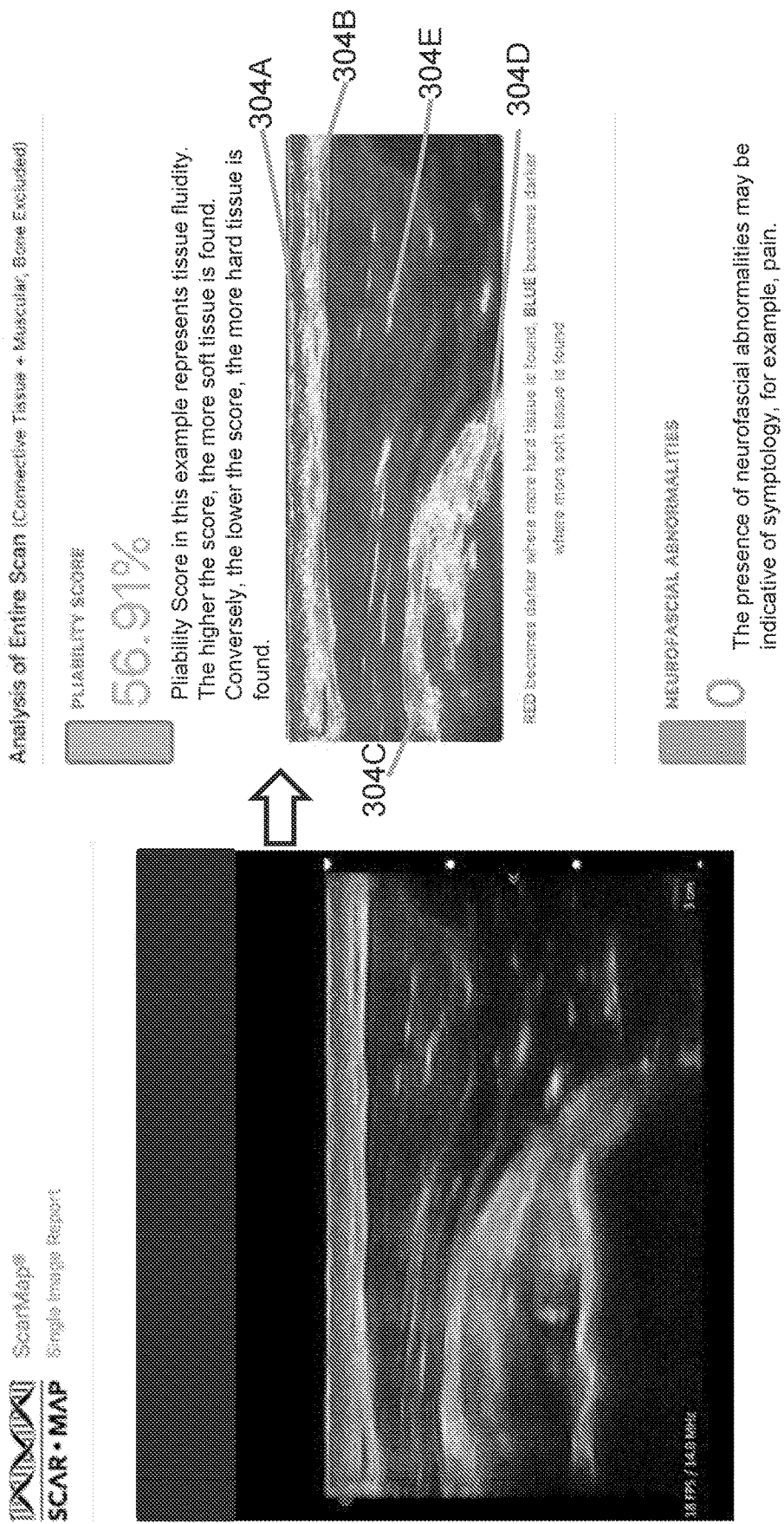

FIGS. 3H and 3I illustrate additional examples in which a computing system (e.g., the computing system 110 executing the neural network module 113b) uses a trained neural network to output information which indicate health of tissue represented by an ultrasound image. More specifically, the trained neural network may output at least a pliability score which indicates pliability, or more specifically fluidity, of connective tissue and muscle tissue represented in the ultrasound image. The pliability score in FIG. 3H may be determined based on an ultrasound image captured from a patient, before the patient has been treated for damaged or stiff connective tissue. The pliability score in FIG. 3I may be determined based on another ultrasound image captured from the same patient, after the patient's connective tissue has been treated. The trained neural network may further indicate whether there is an entrapped nerve in the tissue represented by the ultrasound image, or more specifically whether there is a neurofascial abnormality in the tissue. In an embodiment, the computing system may be configured to identify regions in the ultrasound image that include a sign of damaged tissue, and to identify regions in the ultrasound image which include a sign of healthy tissue. For instance, tissue which is harder or more dense in a particular region may have a greater correlation with damage to the tissue in that region, while tissue which is softer in a particular region may have greater correlation with being healthy in that region. In the example of FIG. 3H, the computing system may identify regions 302A-302F as regions in which the tissue is harder than in surrounding regions, while in the example of FIG. 3I, the computing system may identify regions 304A-304E as regions in which the tissue is harder than in surrounding regions. Further in the example of FIGS. 3H and 3I, the computing system may be configured to represent the regions 302A-302F or 304A-304E with one color (e.g., red), and to represent surrounding regions with another color (e.g., blue). More specifically, the computing system may convert a grayscale version of the ultrasound image to a color version of the ultrasound image. The color version of the ultrasound image may have multiple color components, or more specifically multiple color channels, such as a red channel and a blue channel. The red channel may represent tissue which is relatively hard, and may have intensity values that are based on a level of hardness, with intensity values increasing (or alternatively decreasing) with increasing levels of hardness. The blue channel may represent tissue which is relatively soft, and may have intensity values based on a level of softness, with intensity values increasing (or alternatively decreasing) with increasing levels of softness. In some cases, the computing system may identify the regions 302A-302F or 304A-304D and/or generate the color version of the ultrasound image based on the neural network used to compute the pliability score. In some cases, the computing system may identify the regions 302A-302F or 304A-304D and/or generate the color version of the ultrasound image without relying on the neural network. In such cases, the computing system identify such regions and/or generate the color version of the ultrasound image based on pixel intensity values in the grayscale version of the ultrasound image which is received by the computing system.

In an embodiment, a trained neural network that is configured to output multiple types of information, such as in the example of FIG. 3G, may facilitate more efficient use of computing resources, and thus may provide a technical effect of improving computing efficiency and usage. For instance, training a single neural network to output the pliability scores, to output the information identifying entrapped nerves, and to output the information identifying regions of damaged tissue may reduce an overall amount of training that is needed, and may lead to a neural network that is more accurately trained. Thus, such an embodiment may provide an improvement in computing technology.

Figure 4:
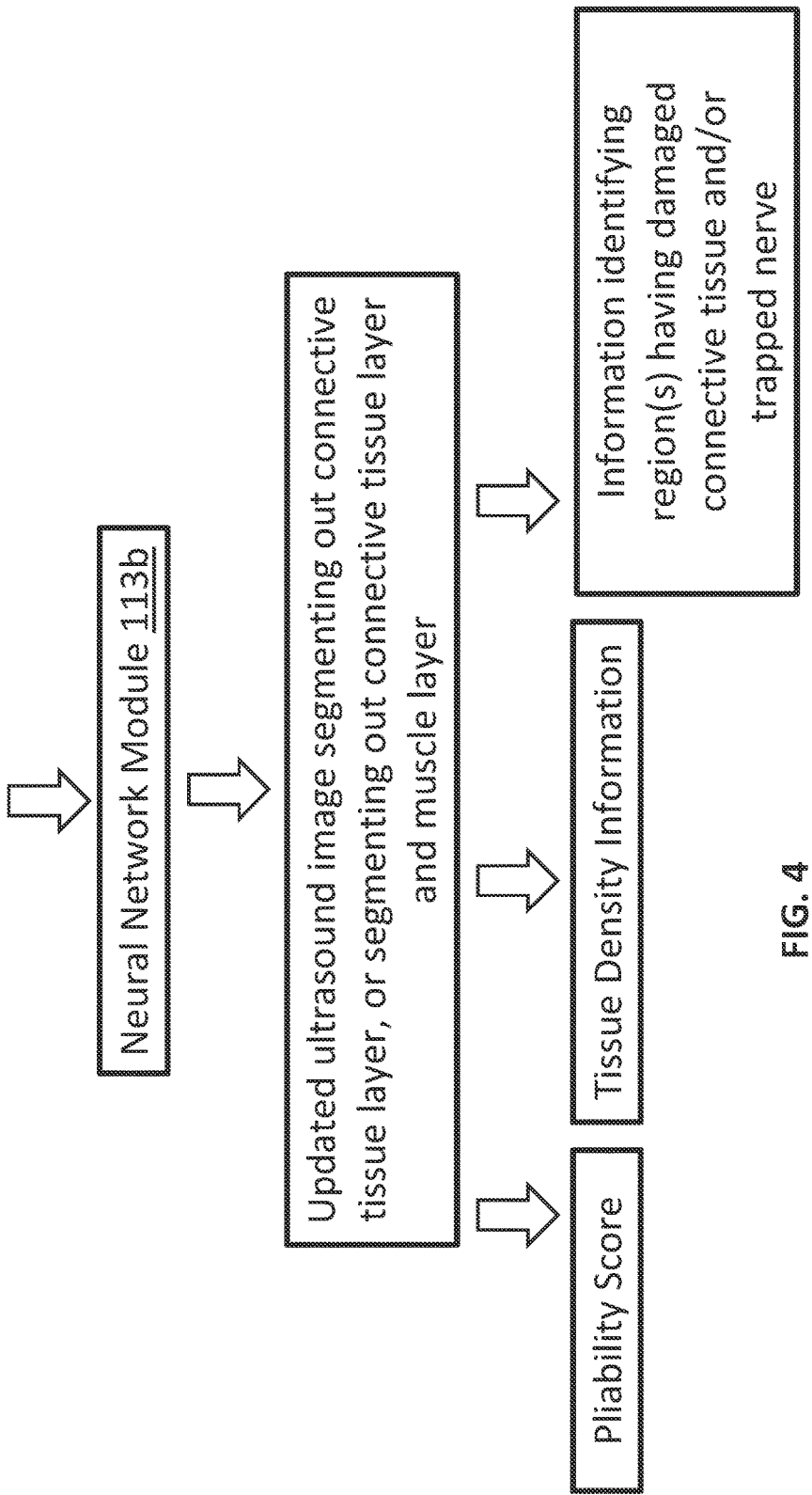
FIG. 4 illustrates a trained neural network that processes an ultrasound image to output an updated ultrasound image that segments out a connective tissue layer, or segments out a connective tissue layer and muscle layer. The updated ultrasound image may remove image data which represents any bone underneath the connective tissue layer and muscle.

In some cases, the trained neural network may be configured to process an ultrasound image that represents not only a connective tissue layer, but also underlying muscle and bone. In these cases, the trained neural network may be configured to isolate the connective tissue layer from a remainder of the image data of the ultrasound image. In other words, the trained neural network may be configured to recognize features which belong solely to the connective tissue layer. For instance, FIG. 4 illustrates an example in which the trained neural network of the neural network module 113b may be configured to process an ultrasound image to remove (e.g., strip or filter out) image data representing any bone in the image and/or muscle, so as to generate an updated ultrasound image that represents only a connective tissue layer. In the embodiment of FIG. 4, the updated ultrasound image may be used to determine one or more of the pliability score, tissue density information, information identifying one or more regions of the updated ultrasound image that represent damaged connective tissue, and/or information identifying one or more regions of the ultrasound image that represent respective one or more locations having an entrapped nerve. In an embodiment, the neural network used to output the updated ultrasound image may be a first neural network, and one or more additional neural networks may be used to output additional information based on the updated ultrasound image. The additional information may be, e.g., the pliability score, the tissue density information, and/or the information identifying region(s) of the updated ultrasound image that represent damaged connective tissue and/or a trapped nerve.

Figure 5A:
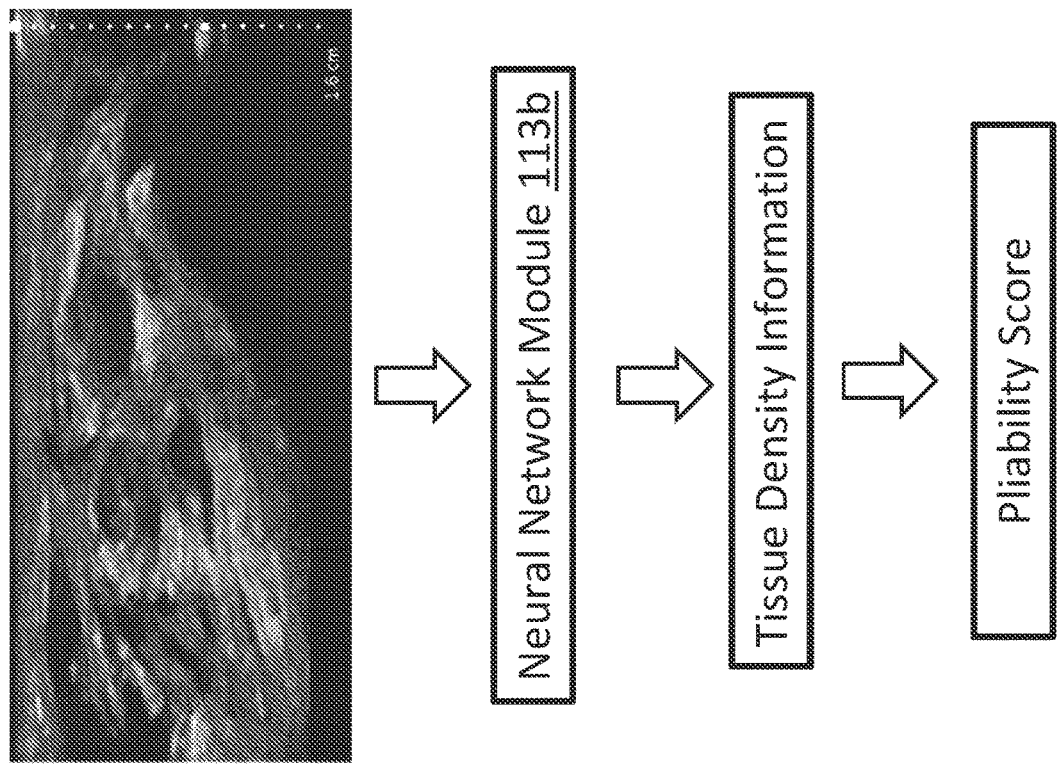
FIGS. 5A and 5B illustrate the use of tissue density information to determine a pliability score.

As stated above with respect to FIG. 3A, one aspect of the embodiments herein relate to determining a pliability score that indicates health of connective tissue. FIG. 5A depicts an embodiment in which the pliability score discussed above is determined based on tissue density information. More particularly, as stated above with respect to FIG. 3A, the pliability score may be based on or may be affected by a ratio between how much healthy connective tissue is present in the connective tissue layer and how much damaged connective tissue is present in the connective tissue layer. In the example of FIG. 5A, the amount of healthy connective tissue and/or the amount of damaged connective tissue may be determined based on tissue density information, which may be outputted by the trained neural network of the neural network module 113b. For instance, the tissue density information may indicate how much of the connective tissue layer is occupied by one or more clusters of material which has density higher than a defined threshold. These clusters may be determined to represent tissue that likely has calcification and thus likely has damage. Further, portions of the connective tissue layer which has a density that does not exceed the defined threshold may be determined to likely be healthy connective tissue. In an embodiment, the tissue density information in FIG. 5A may be determined via a first neural network, and the pliability score may be determined based on the tissue density information. The determination of the pliability score from the tissue density information may be based on a second neural network, or based on some other technique.

Figure 5B:
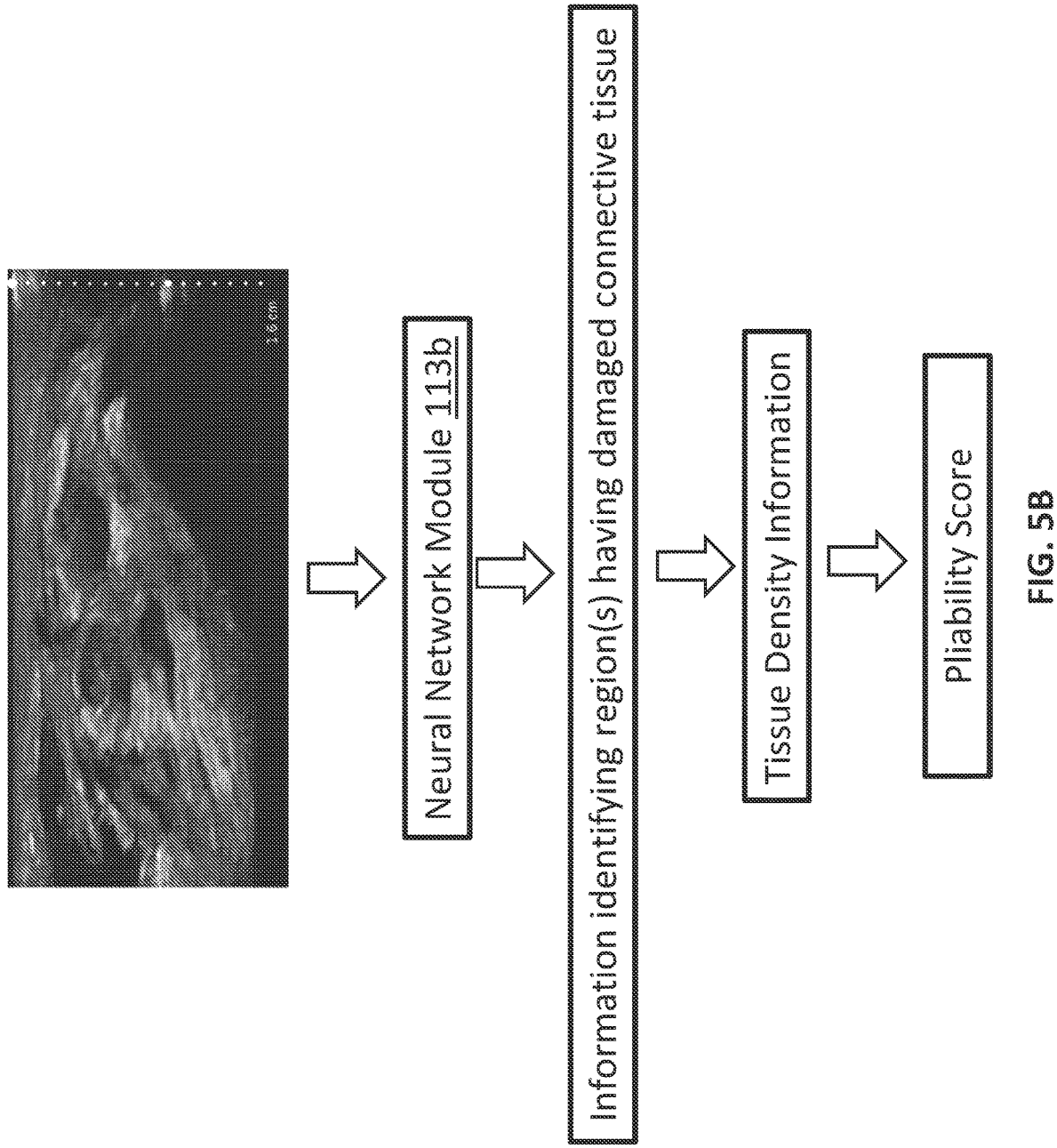
Figure 5C:
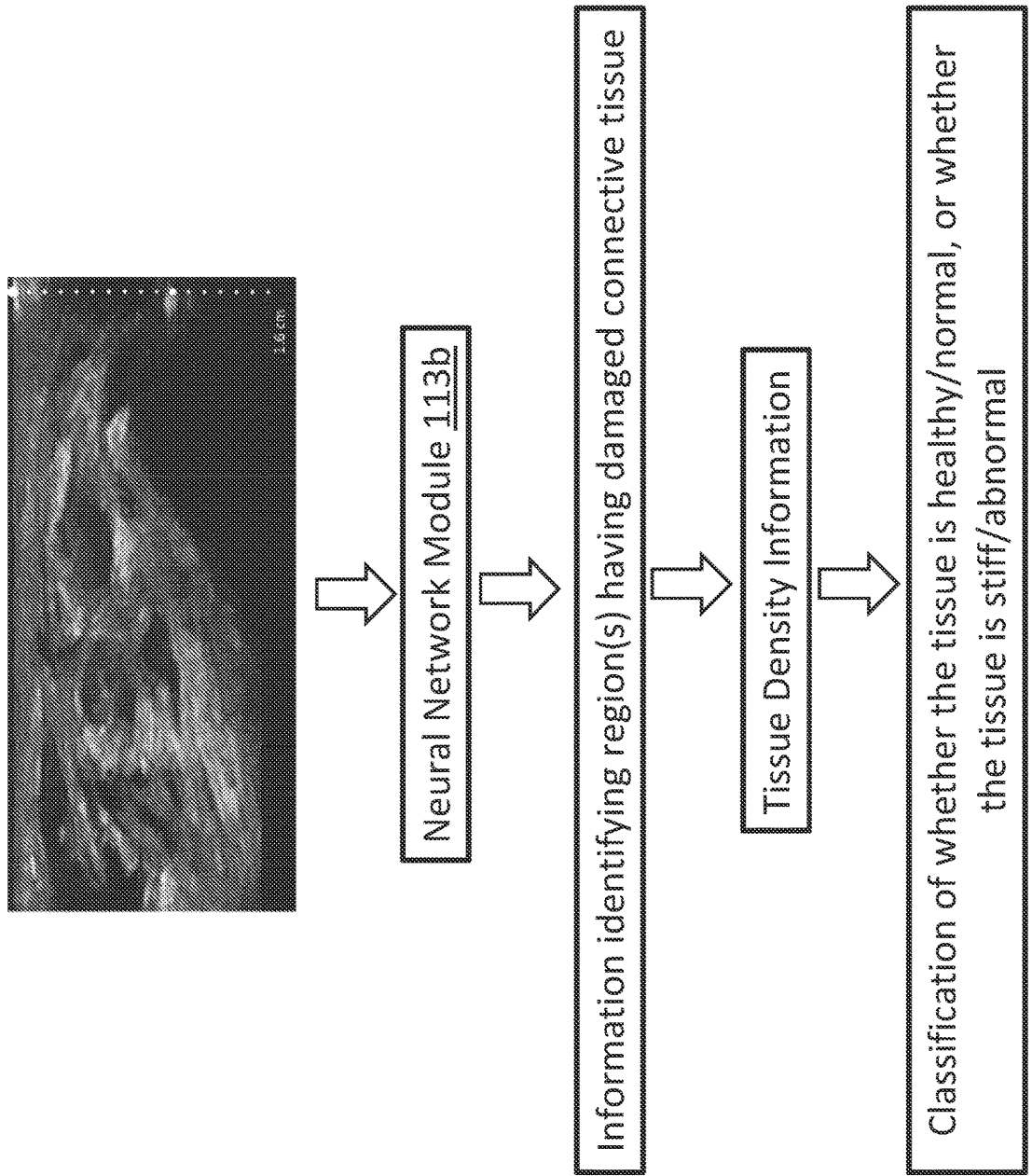
FIG. 5C illustrates the use of tissue density information to classify whether connective tissue is normal/healthy, or whether the connective tissue is abnormal/stiff.

In some cases, the tissue density information may be determined based on information identifying damaged connective tissue in a connective tissue layer. For example, FIGS. 5B and 5C illustrate embodiments in which the trained neural network of the neural network module 113b is configured to identify one or more regions of an ultrasound image that represent damaged connective tissue (or, more generally, to identify one or more regions of interest). These one or more regions may each have, e.g., a cluster with a density that exceeds a defined threshold. The tissue density information may indicate, e.g., how much of the connective tissue layer is occupied by the one or more regions, and/or an overall density of the connective tissue layer. In some cases, the one or more regions of interest identified by the trained neural network may additionally or alternatively represent one or more respective locations of the connective tissue layer at which there is likely an entrapped nerve. The tissue density information may be used to determine a pliability score, as illustrated in FIG. 5B, or a classification of whether tissue density is normal or abnormal, as illustrated in FIG. 5C. In the example of FIGS. 5B and 5C, the one or more regions may be identified via a first neural network, and a second neural network may use the identified one or more regions to determine the tissue density information. The tissue density information may be used to determine the pliability score or the classification via a third neural network.

In some implementations, one or more of the embodiments in FIGS. 3A through 5C may be combined. For example, the neural network module 113b may be configured to use a first trained neural network to generate an updated ultrasound image which represents a connective tissue layer, and not a muscle layer nor bone adjacent to the connective tissue layer. The neural network module 113b may be configured to use the first trained neural network, or a second trained neural network to determine tissue density information from the updated ultrasound image, and/or areas of interest. The areas of interest may include regions of the updated ultrasound image which show irregularity, such as regions representing clusters with a density that exceed a defined threshold, clusters having a depth-to-width ratio that exceed 1, clusters having a non-symmetric shape, a value or range of values (e.g., pliability score) indicative of health of the connective tissue, a classification of whether the connective tissue is normal or abnormal, and/or regions showing non-contiguous lines. In some cases, the neural network module may be configured to also output, based on the updated ultrasound image and another trained neural network (e.g., a third trained neural network), regions which represent locations at which there is likely an entrapped nerve.

Figure 6:
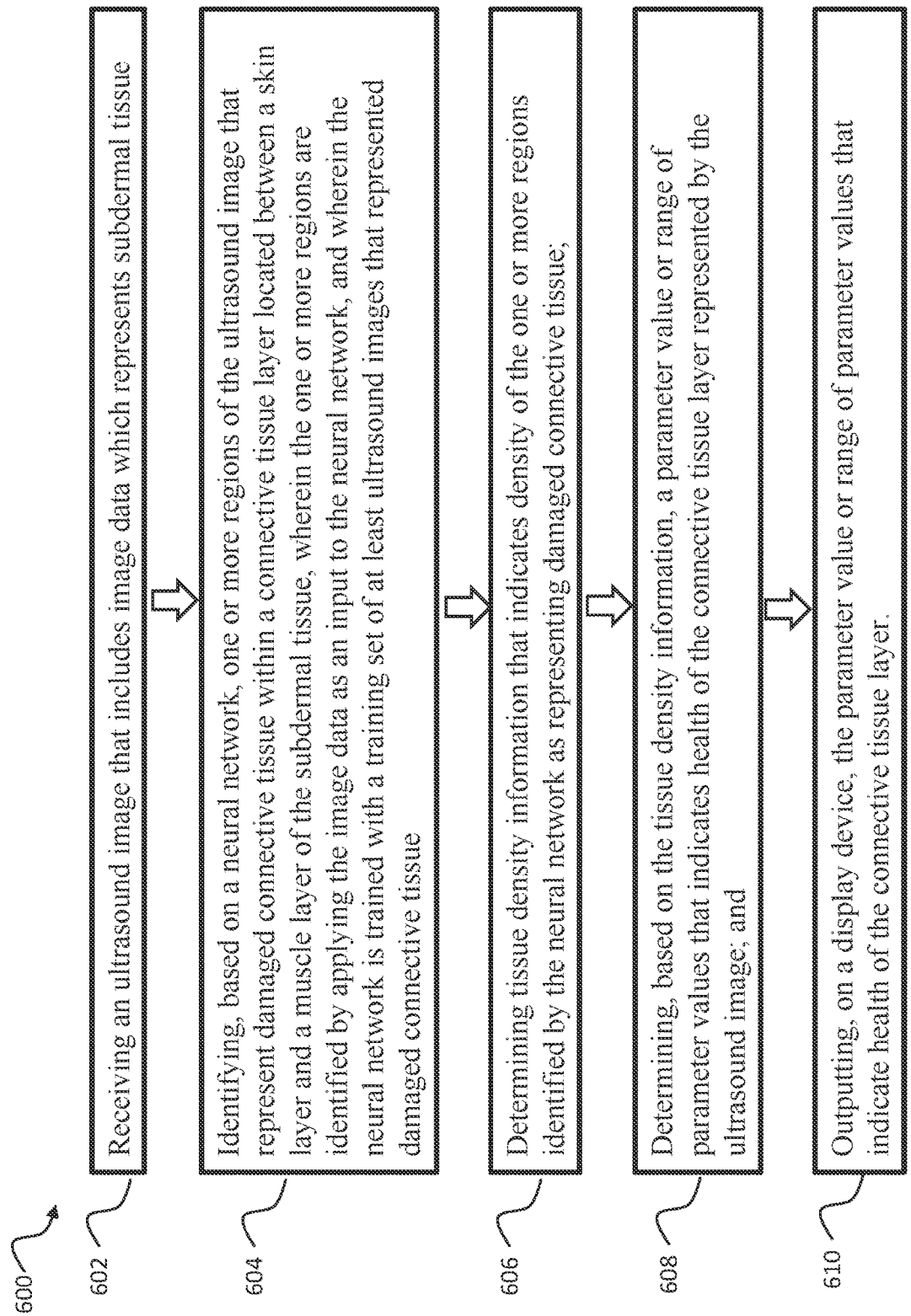
FIG. 6 depicts a flow diagram of an example method for processing an ultrasound image with a neural network to evaluate health of a connective tissue layer.

FIG. 6 illustrates example steps of a method 600 for assessing health of connective tissue in a connective tissue layer. The method 600 may be performed by a computing system, such as the computing system 110, or more specifically by its processing circuit 111. In an embodiment, the method 600 may begin at step 602, in which the computing system 110 receives an ultrasound image that includes image data which represents subdermal tissue. In some cases, the ultrasound image may be based on sensor data that senses tissue which is within 10 cm of skin surface, and which does not sense deeper tissue (e.g., does not sense internal organs such as lungs). In one example, the computing system may output an instruction (e.g., via a display device) to instruct a user to administer the ultrasound per body part (e.g., arm, leg, shoulder) with a uniform depth (e.g., 4 cm for the knee) and uniform administration (e.g., horizontal and always administering the ultrasound downwards away from the heart).

In an embodiment, the ultrasound image may be received directly from an ultrasound scanning system (e.g., ultrasound scanning system 120) or may be received from a storage device, or more generally a non-transitory computer-readable medium (e.g., non-transitory computer-readable medium 113). The ultrasound image may be a standalone image (e.g., a still image), or may be a frame of a video feed. In some cases, the ultrasound image may be a grayscale image which has a plurality of pixels, wherein each of the pixels has an image intensity value between a defined minimum value (e.g., zero) and a defined maximum value (e.g., 255). A higher image intensity value may cause the pixel to, e.g., appear more white, while a lower image intensity value may cause the pixel to, e.g., appear more dark.

In step 604, the computing system may identify, based on a neural network, one or more regions of the ultrasound image that represent damaged connective tissue within a connective tissue layer, wherein the connective tissue layer is located between a skin layer and a muscle layer of the subdermal tissue. In an embodiment, the one or more regions may be identified by applying the image data as an input to the neural network. The neural network may have been trained with a training set of at least ultrasound images that represented damaged connective tissue, so as to be able to recognize damaged connective tissue from an ultrasound image. In one example, the neural network may have been trained to recognize clusters in the ultrasound image which have a high density and/or an irregular structure (e.g., a non-symmetric shape or non-laminar structure). The high density and/or irregular shape may, e.g., indicate locations of calcification that results from scarring of damaged connective tissue. As discussed below in more detail, the neural network may additionally or alternatively have been trained to recognize regions of the ultrasound image that represent respective locations at which there is an entrapped nerve or channel blockage.

In an embodiment, step 604 may be preceded by a step in which the computing system determines whether the ultrasound image is usable. For instance, the computing system may determine whether the ultrasound image is too dark (e.g., due to error by the person administering the ultrasound scan).

In an embodiment, the computing system 110 may use the trained neural network to process the ultrasound image in chunks, and stitch the result together. Processing the ultrasound image in this manner may reduce the number and/or size of filters needed in the neural network.

In step 606, the computing system may determine tissue density information that indicates density of the one or more regions identified by the neural network as representing damaged connective tissue. For example, the tissue density information may indicate an overall density of the connective tissue layer, and/or may indicate how much of the connective tissue layer is occupied by one or more high-density clusters, wherein each of the high-density clusters is a cluster of the connective tissue layer having a density that is higher than a defined threshold.

In step 608, the computing system may determine, based on the tissue density information, a parameter value or range of parameter values that indicates health of the connective tissue layer represented by the ultrasound image. In an embodiment, the parameter value or range of parameter values may be a pliability score that indicates mobility (or, inversely, stiffness) of the connective tissue layer represented by the ultrasound image.

In step 610, the computing system outputs, on a display device (e.g., display device 115), the parameter value or range of parameter values that indicate health of the connective tissue layer.

In some cases, the neural network discussed above may be a convolutional neural network that identifies and segments out (e.g., extracts) the connective tissue layer in the ultrasound image, as illustrated by the block diagram of FIG. 4. For example, the neural network may be configured to output an updated ultrasound image that strips out the bone. In such an example, tissue density information, the pliability score, and/or the areas of interest (including regions representing damaged connective tissue) may be determined from the updated ultrasound image. In an embodiment, the convolutional neural network may have been trained from manually-labeled ultrasound images. Segmenting out the connective tissue layer may allow assessment of the ultrasound image to focus on the connective tissue layer, rather than all layers sensed by the ultrasound image. More particularly, segmenting out the connective tissue layer may allow an effect of an underlying bone on the ultrasound image to be removed, so that the computing system 110 may focus on identifying damage specifically within the connective tissue layer. The depth of the connective tissue layer may be influenced by inflammation, dehydration, and other factors (e.g., calcifications, entrapped nerves, fusion with the dermis layer). In an embodiment, the neural network may be a convolutional neural network, a corner classification neural network, a recurrent neural network, an autoencoder, a generative adversarial neural network (GAN). In some cases, the neural network may be used in combination with unary coding or any other coding.

Figure 7A:
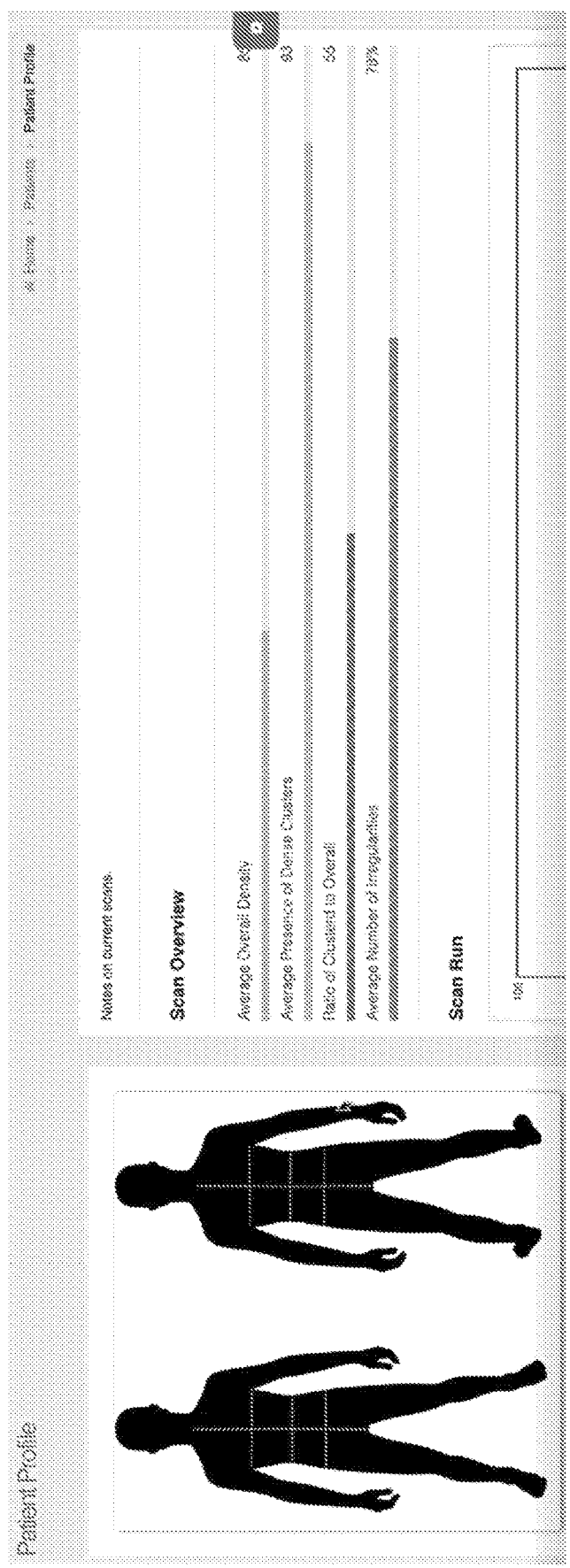

In some cases, the computing system may output the tissue density information on the display device. For example, FIG. 7A depicts an example in which a display device outputs tissue density information that indicates an average overall density of a patient's connective tissue layer, and an average presence of dense clusters. In an embodiment, the average overall density of the tissue density layer may measure, e.g., a density of tissue material forming the connective tissue layer and/or how much of the connective tissue layer is not fluid. In an embodiment, the average presence of dense clusters may be a spatial density that measures how much of the connective tissue layer is occupied by clusters which have a density that is higher than a defined threshold. In some cases, these clusters may each be a cluster identified by the trained neural network as a region representing damaged connective tissue. As depicted in FIG. 7A, the display device may further output an average number of irregularities. Each of the irregularities may refer to, e.g., a region of the ultrasound image identified by the trained neural network as representing damaged connective tissue, and the number of irregularities may refer to how many regions have been identified by the neural network as representing damaged connective tissue.

Figure 7B:
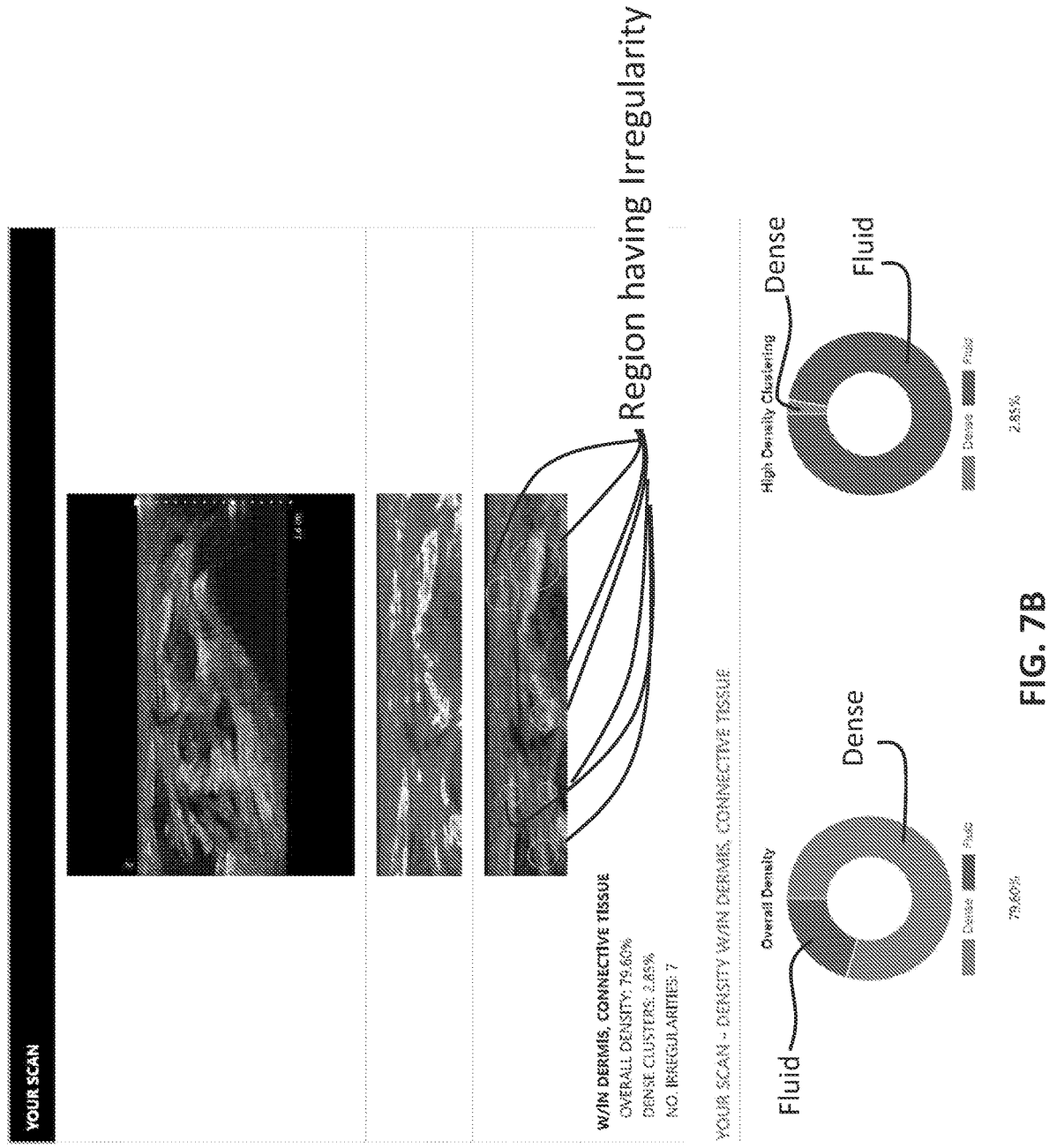

FIG. 7B depicts another example of output by a display device based on information output by a trained neural network. More particularly, the display device may output an overall density of the connective tissue layer. This information may more specifically indicate how much of the connective tissue layer comprises tissue material and how much of the connective tissue layer is not fluid. The display device may further output an amount of high-density clustering in the connective tissue layer. This information may indicate how much of the connective tissue layer is occupied by dense clusters. Additionally, the output on the display device may further indicate how many irregularities have been identified by the neural network based on the ultrasound image. As stated above, the irregularities may refer to regions of the ultrasound image which have been identified by the neural network as representing damaged tissue.

Figure 8A:
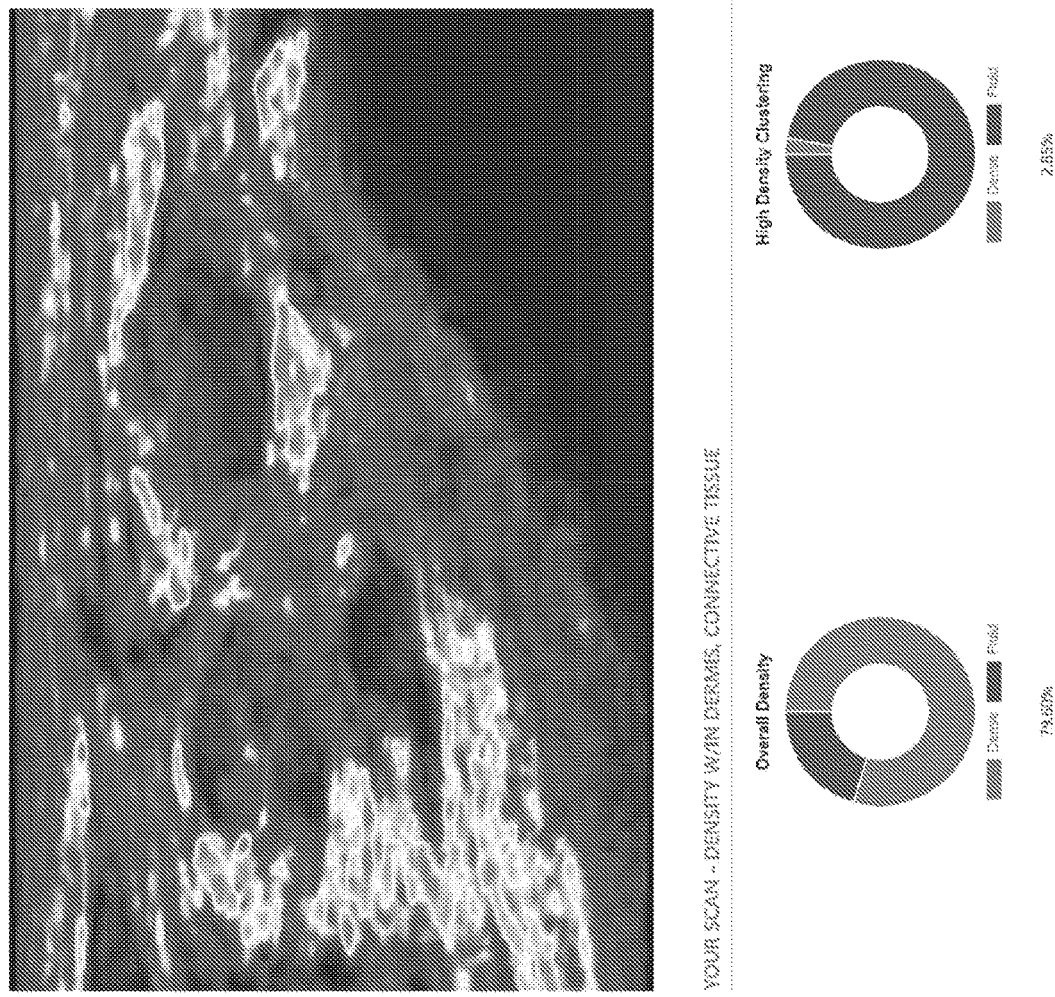

FIGS. 8A and 8B provide another example of the output that is generated by processing an ultrasound image using a neural network. Similar to FIG. 7B, the output illustrated in FIG. 8A may indicate an overall density and an amount of high-density clustering in the connective tissue layer, wherein the output may be generated based on an ultrasound image. The output in FIG. 7B may further include an updated ultrasound image that uses visual features (e.g., colors) to identify regions representing damaged connective tissue. For instance, these regions may correspond with clusters having a density that exceed a defined threshold. In such an instance, the output may include an updated ultrasound image that uses a first color to identify regions that represent such clusters, wherein the first color is different from all other color(s) used for remaining portions of the updated ultrasound image.

As depicted in FIG. 8B, the output may further identify information that indicate health of muscle tissue. As stated above, the techniques discussed above for the connective tissue layer may also be used for the muscle layer. Thus, in the example of FIG. 8B, the output may indicate tissue density information (e.g., overall density, or average presence of dense clusters) for not only the connective tissue layer, but also for a layer of muscle beneath the connective tissue layer. As shown in the figure, the output may further indicate an average number of irregularities within the layer of muscle.

Figure 9:
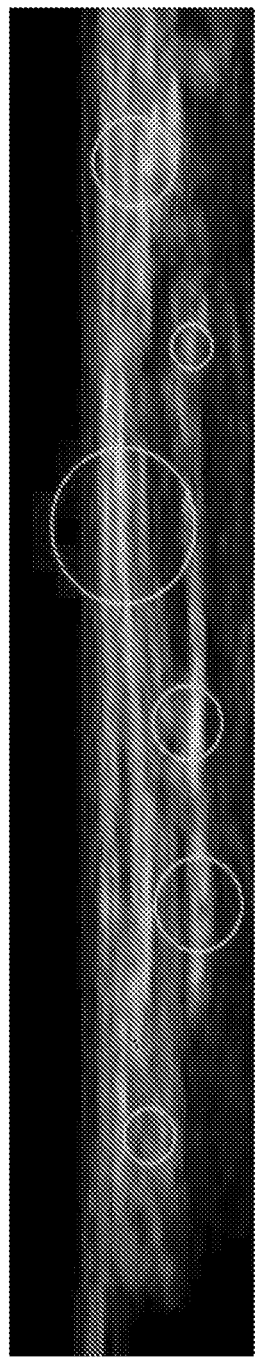
FIG. 9 depicts an example of information which identifies one or more regions of an ultrasound image that may represent damaged connective tissue.

As stated above with respect to FIG. 3C, the trained neural network in some embodiments of the present application may output information identifying one or more regions that represent damaged connective tissue. FIG. 9 illustrates a graphical example of such information. More particularly, the figure presents an ultrasound image added with visual features or visual identifiers (e.g., circles) that each indicates a region of interest. The region of interest may identify, e.g., presence of calcifications, adhesions or other scarred and damaged tissue which could lead to blockages of the connective tissue, lack of mobility, and stiffness. In an embodiment, the region of interest may identify presence of an entrapped nerve(s), and/or indicate blockage of a fluid channel in the connective tissue layer.

Figure 10A:
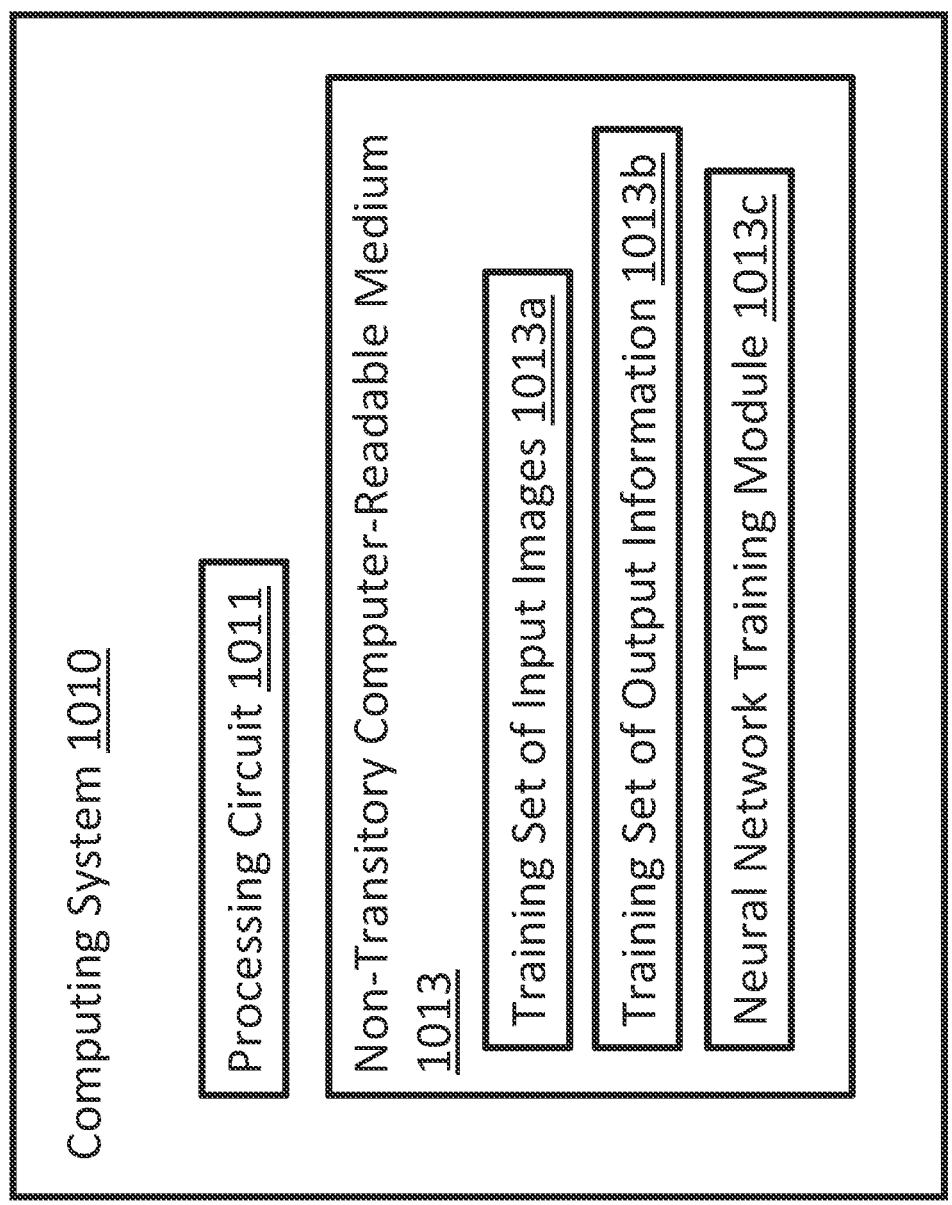
FIG. 10A depicts a computing system for training a neural network to process an ultrasound image.

FIG. 10A depicts a computing system 1010 that is configured to train a neural network to output the information discussed above. In an embodiment, the computing system 1010 may include a processing circuit 1011 that is configured to execute a neural network training module 1013c. The neural network training module 1013c may be configured to train a neural network based on a training set of input ultrasound images 1013a and a training set of output information 1013b. In an embodiment, the neural network training module 1013c may rely on, e.g., TensorFlow and/or Tensor RT to train the neural network. The training set of output information may include, e.g., one or more pliability scores, tissue density information, information identifying one or more regions representing damaged connective tissue, information identifying one or more regions representing respective one or more locations at which there is an entrapped nerve, and/or an updated ultrasound image that includes image data representing only connective tissue and/or muscle tissue (and not representing bone or other structure under the muscle tissue). In an embodiment, the neural network may be trained on a large set of ultrasound images which reflect a broad range of ages, demographics, a range of connective tissue health (e.g., healthy connective tissue and unhealthy connective tissue), and clinical validation from a variety of trained ultrasound experts.

Figure 10B:
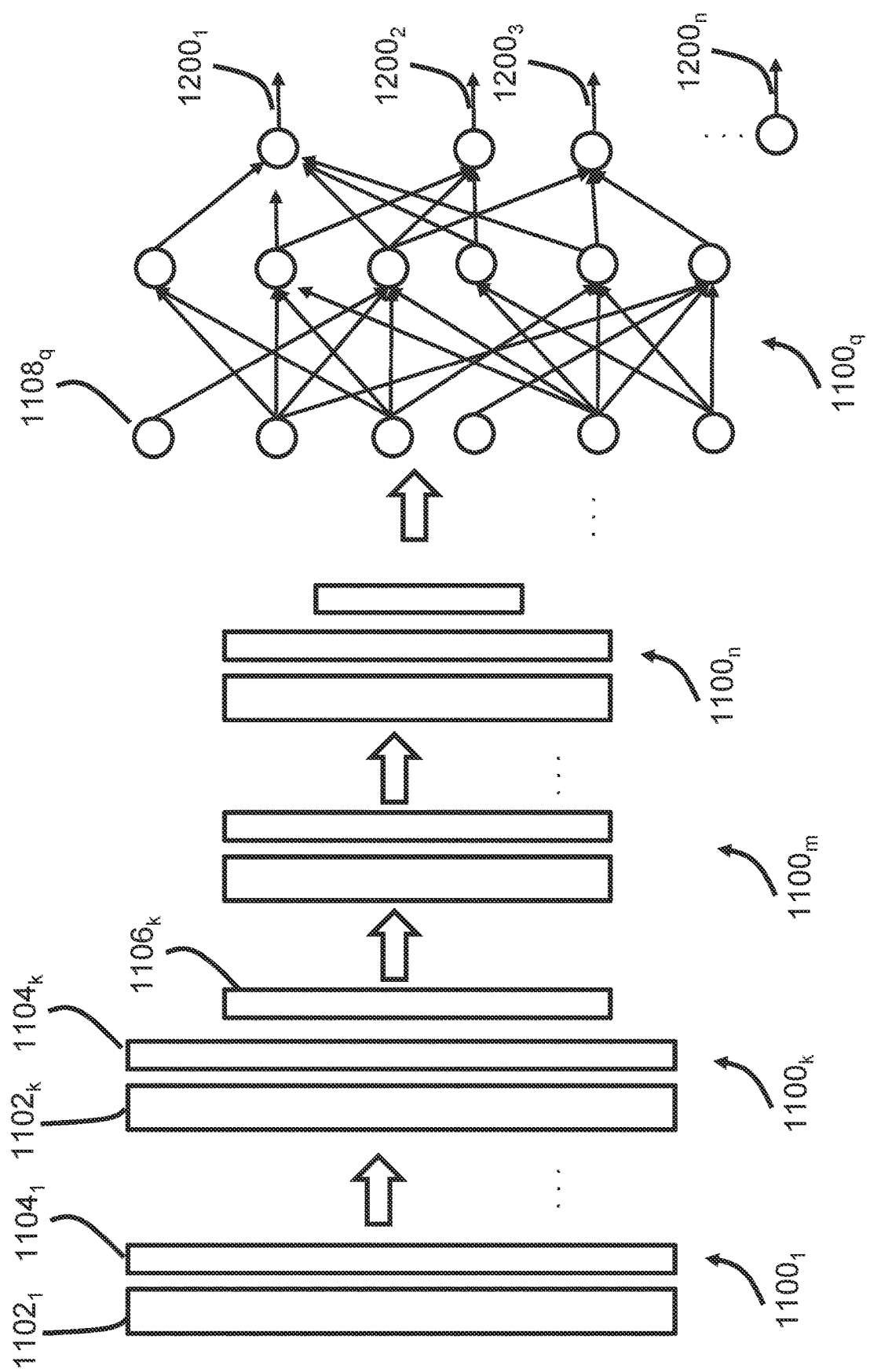
FIG. 10B depicts an example neural network that may be trained to process an ultrasound image and to output one or more types of information, according to an embodiment hereof.

FIG. 10B provides an example neural network which may be trained by the neural network training module 1013c. In this example, the neural network may include a sequence of layers, such as convolutional layers $1100_1$ through $1100_n$ and one or more fully connected layers, such as layer $1100_q$. In some cases, each of the convolutional layers $1100_1$ through $1100_n$ may include a convolutional filter, such as convolutional filter $1102_1$ or $1102_k$, and a rectification layer, such as rectification layer $1104_1$ or $1104_k$. The convolutional filter $1102_1$ may be configured to perform a convolution on pixels of an ultrasound image, while convolutional filters in other layers may be configured to perform a convolution on output of a previous convolutional layer. In some implementations, the rectification layer in a convolutional layer may be configured to apply a rectification function to an output of a convolutional filter in that layer. The rectification function may, e.g., set a particular value to zero if the value is below a defined threshold. Examples of the rectification function include, e.g., a sigmoid function or a ReLU function. In an embodiment, some of the convolutional layers may include a max-pooling layer, such as $1106_k$. The max-pooling layer may be configured to consolidate a patch of pixels from the rectification layer into a single pixel, and may have an effect to facilitating an ability of subsequent layers to detect larger image features. In an embodiment, the neural network may include a fully connected layer, such as layer $1100_q$, which may include at least one layer of perceptrons that are configured to process an output from a previous layer of perceptrons. In an embodiment, the neural network may have one or more outputs, such as outputs $1200_1$ through $1200_n$. As an example, outputs $1200_1$ through $1200_3$ may be a first pliability score, a second pliability score, and a third pliability score, respectively. In another example, the outputs may additionally or alternatively include values which identify a region of interest, such as a region showing a sign of damaged tissue, and/or values which indicate presence of an entrapped nerve.

Figure 11A:
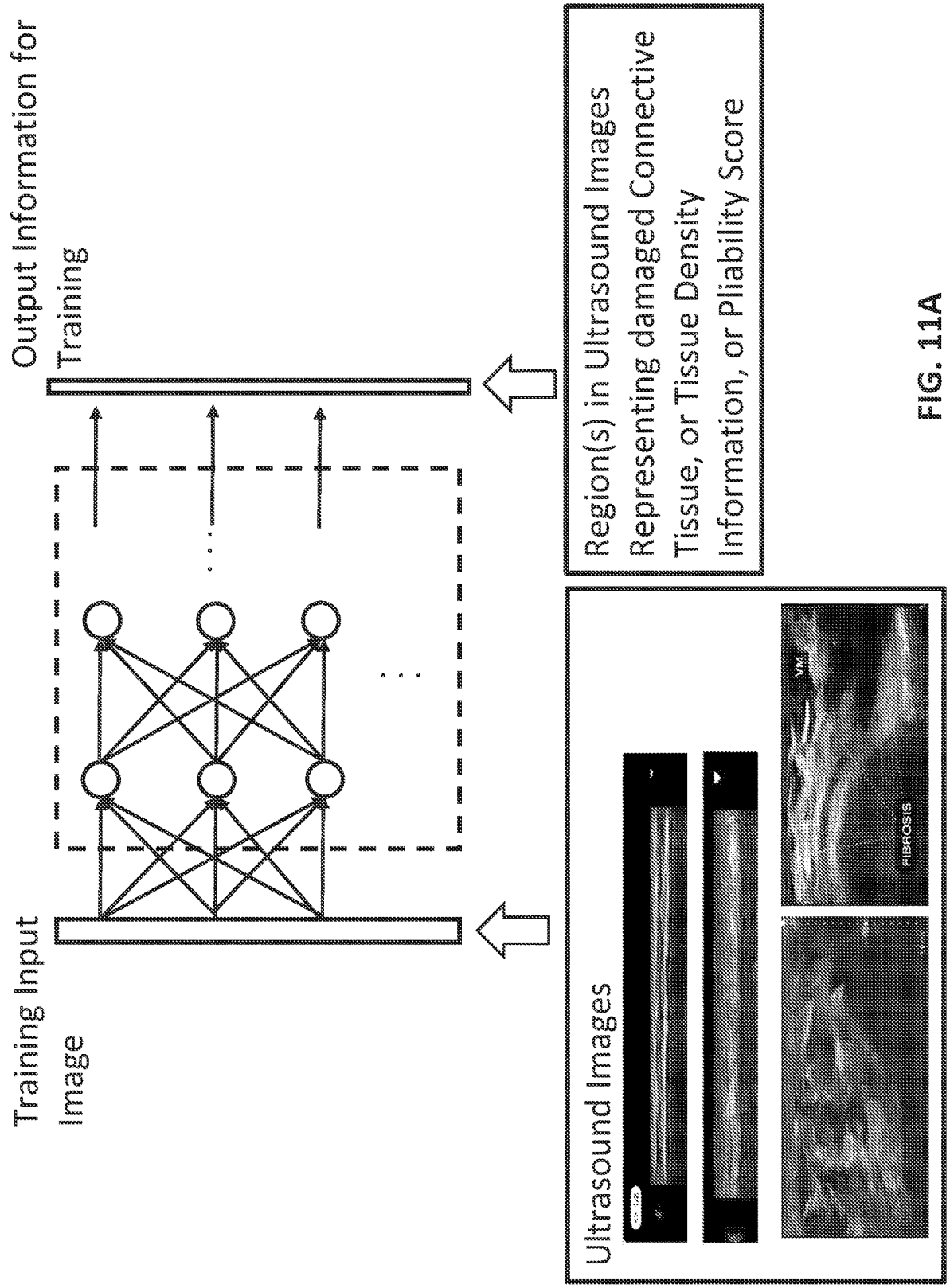
FIG. 11A provides a block diagram that illustrates training of a neural network to process an ultrasound image.
Figure 11B:
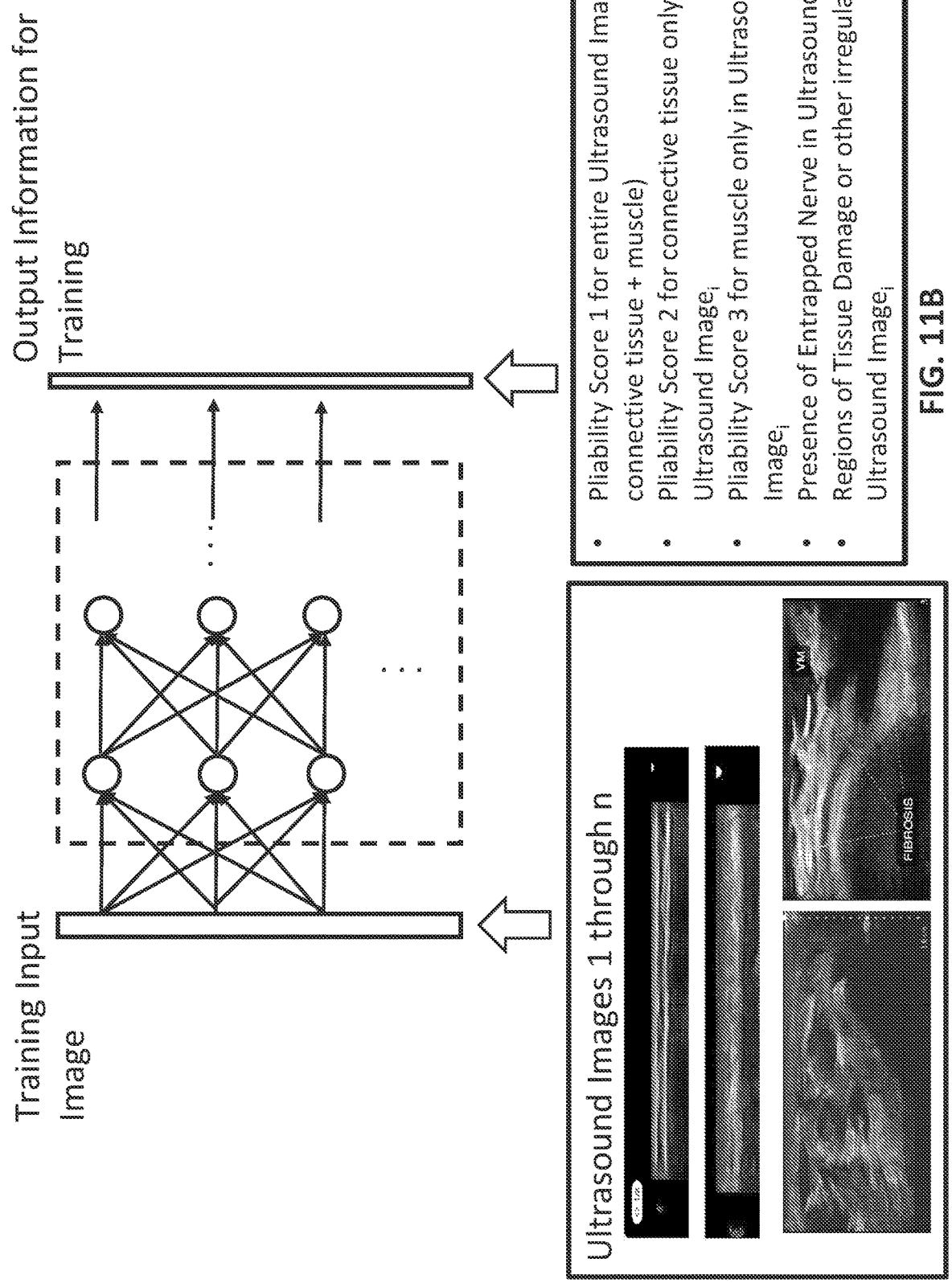
FIG. 11B provides a block diagram that illustrates training of a neural network to process an ultrasound image.

FIGS. 11A and 11B present graphical examples of a neural network, such as the neural network of FIG. 10B, being trained. More particularly, training the neural network may involve adjusting weights based on input ultrasound images and a desired output. The weights may belong to a weighted sum operation of a plurality of components, wherein the weighted sum operation may be represented by convolutional filters and perceptrons. In some implementations, the pliability scores used for training the neural network may be provided by a clinician or other doctor of patients seeking treatment for stiffness of limited mobility in their muscles and/or connective tissue. In some instances, the pliability scores used for training may have been determined based on analyzing the ultrasound images. For example, the pliability scores may be determined (e.g., manually) based on how much calcification or other scarring in the connective tissue is indicated by the ultrasound images. In some instances, the pliability scores used for training may have been determined without relying on the ultrasound images. For example, they may be determined based on information reported by a patient, such as a level of pliability or stiffness in connective tissue, pain being experienced by the patient in or around connective tissue, or the patient experiencing a lack of mobility or pliability in the connective tissue. In some instances, the pliability scores used for training may have been determined based on a combination of the examples discussed above. In the above example, the ultrasound images used for training may be generated from the patients before and after treatment. The ultrasound images which are generated before treatment may be defined as representing damaged connective tissue (or other subdermal tissue), and may be assigned or otherwise associated with low pliability scores, and the ultrasound images which are generated after a successful treatment may be defined as representing healthy tissue, and may be assigned or otherwise associated with high pliability scores.

Figure 12A:
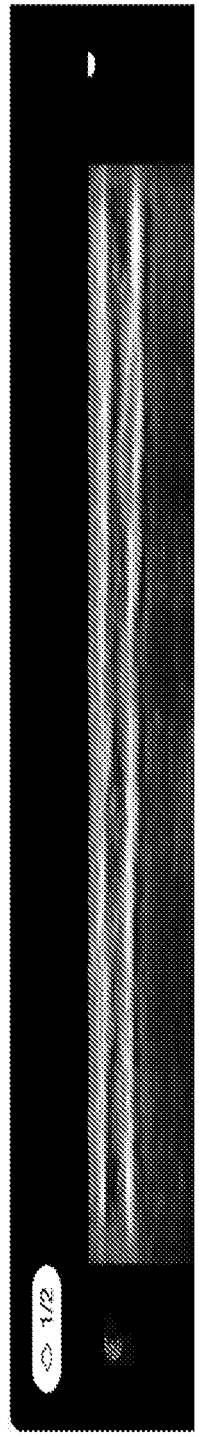
FIG. 12A provides an example of an ultrasound image that represents healthy connective tissue within a connective tissue layer, wherein the ultrasound image is used to train a neural network.
Figure 12B:
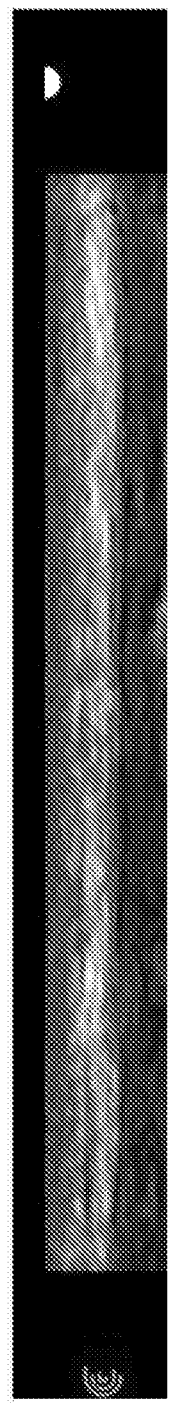
FIG. 12B provides an example of an ultrasound image that represents damage within a connective tissue layer, wherein the ultrasound image is also used to train the neural network.

In an embodiment, the neural network may be trained to recognize one or more regions having a density associated with damaged tissue, such as a density which exceeds a defined threshold, as discussed above. In an embodiment, the neural network may be trained to recognize a structure associated with damaged tissue. Such a structure may exhibit less organization than healthy connective tissue. For example, FIG. 12A illustrates an ultrasound image representing healthy connective tissue. The image shows an organized, laminar structure in which the connective tissue forms clearly, distinguishable borders around a fluid channel. The fluid channel may be responsible for the diffusion and transport of nutrients through the body and elimination of debris. FIG. 12B depicts an ultrasound image representing damaged connective tissue. The ultrasound image in FIG. 12B lacks a clear distinguishable fluid channel. Thus, the figure may represent fluid blockage.

Figure 13A:
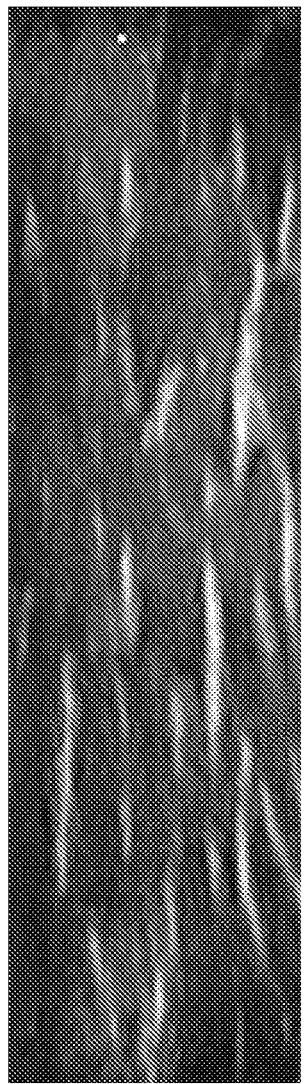
FIG. 13A provides an example of an ultrasound image that represents healthy muscle tissue, wherein the ultrasound image is used to train a neural network.
Figure 13B:
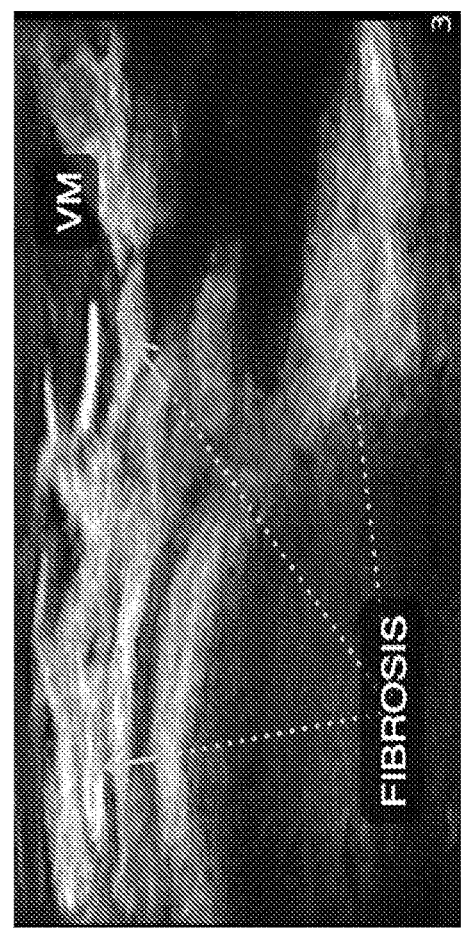
FIG. 13B provides an example of an ultrasound image that represents damaged muscle tissue, wherein the ultrasound image is used to train a neural network.

FIG. 13A depicts an example of an ultrasound image that represents healthy muscle tissue, while FIG. 13B depicts an example of an ultrasound image that represents damaged muscle tissue (e.g., muscle tissue having fibrosis). More particularly, the ultrasound image in FIG. 13A represents tissue which has relative low density, as indicated by the lower image intensity (i.e., lower level of brightness) of the ultrasound image. Further, the ultrasound image in FIG. 13A further depicts a more laminar structure. By comparison, the ultrasound image in FIG. 13B represents muscle tissue that is more disorganized. The figures in FIGS. 13A and 13B may be used to train a neural network for identifying damage within the muscle tissue.

Figure 14:
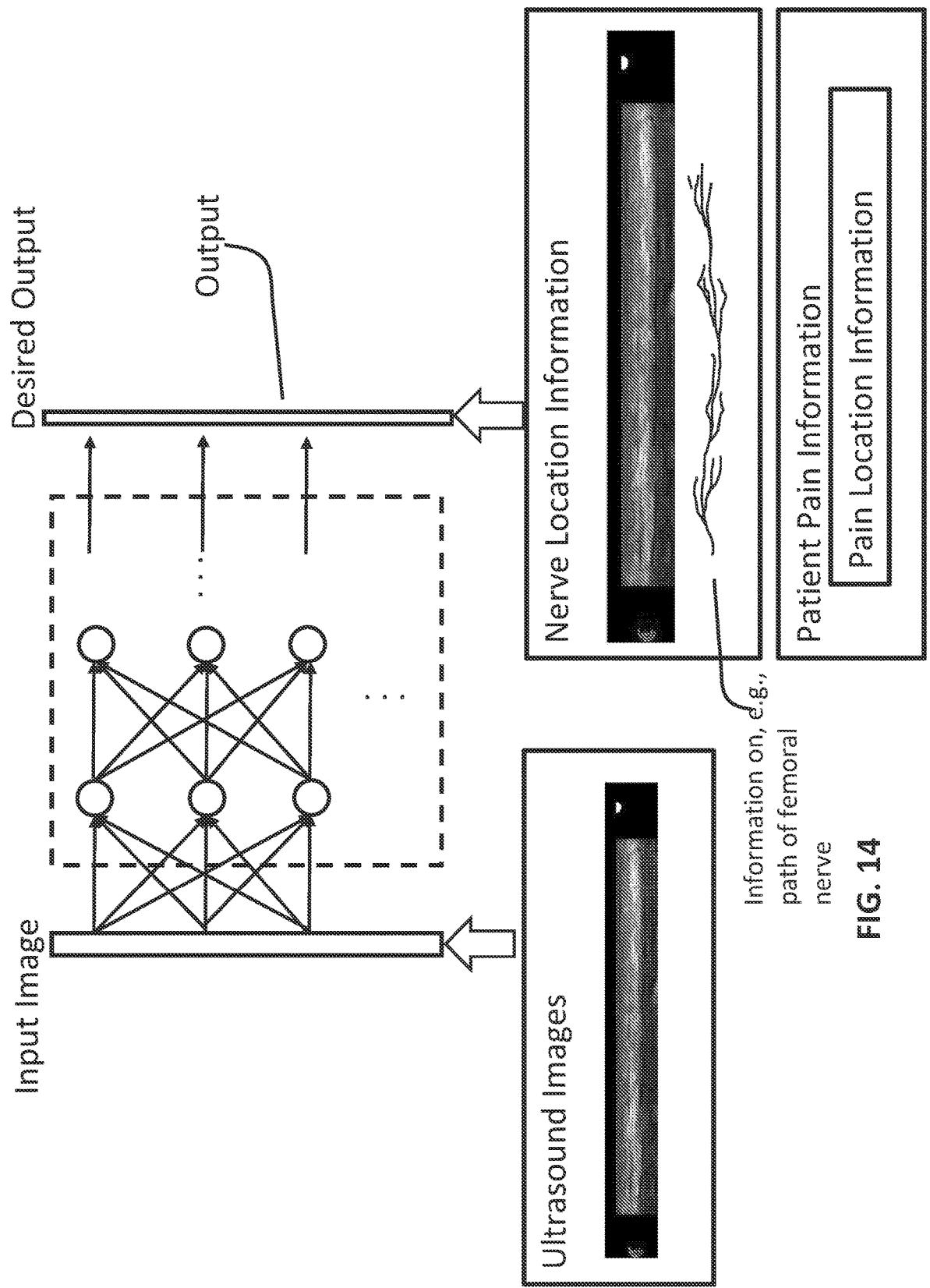
FIG. 14 illustrates the training of a neural network to recognize one or more regions which represent locations within a connective tissue layer.

In some cases, subcutaneous nerves may travel across the layer and can become ensnared or entrapped in the connective tissue via adhesion. FIG. 14 illustrates the training of a neural network to recognize a region of an ultrasound image that represents a location within a connective tissue layer at which there is an entrapped nerve. In an embodiment, the neural network of FIG. 14 may be trained based on known nerve location information and patient pain information. The patient pain information may indicate, for example, whether a patient on whom an ultrasound scan is being performed is experiencing pain, and/or a location of the pain. In some cases, the pain may indicate the presence of an entrapped nerve. The location of the entrapped nerve may be inferred based on the location of the pain, and/or based on the nerve location information. For example, the nerve location information may indicate a known path of a nerve (e.g., femoral nerve or ulnar nerve) through a body part represented by the ultrasound image. In some cases, a location at which the nerve is entrapped may be a location at which there is damaged tissue or channel blockage (which may be identified manually, or may by identified the neural network after it has been trained to recognize tissue damage), and at which the known path of the nerve runs through that location. In some embodiments, this location may be determined manually and used to train the neural network.

Figure 15:
FIG. 15 illustrates the connective tissue layer at which there is an entrapped nerve.

FIG. 15 depicts information that may be used to train the neural network (such as the neural network of FIG. 14) to identify a region in an ultrasound image that represents an entrapped nerve. More specifically, the information may include an ultrasound image and an indication of whether there is an entrapped nerve, as well as a location of the entrapped nerve. In the example of FIG. 15, an inflamed nerve may be identified as the entrapped nerve. In some cases, a location of the inflamed nerve may have been inferred or otherwise determined (manually or automatically) based on known location information for a nerve. For instance, it may be known that the nerve travels in a particular plane of the connective tissue, and this information may be used to infer a location of the inflamed nerve. The location may be used to train the neural network.

In an embodiment, the neural network may be trained to identify a feature of an ultrasound image, such as one or more of: morphology, spiculation, depth-to-width ratio, elliptic-normalized circumference (ENC), shape, presence or absence of calcification, posterior shadow or posterior echo, echo characteristic, slope, and/or whether the tissue is contiguous in nature. In some cases, the neural network may be trained to output an annotated version of the ultrasound image to present the identified feature.

In an embodiment, the morphologic feature may indicate a shape/pattern of the connective tissue layer. The spiculation feature may reflect a smoothness of the layer margin. The depth-to-width ratio may be an active feature for the classification of soft tissue lesions. The depth may refer to as a largest difference between the y-axis values of two points on the margin of the scar. The width may refer to a largest difference between the x-axis values of two points on the margin of the scar. In an embodiment, a neural network may be trained to associate a cluster having a depth-to-width ratio (which may also be referred to as a height-to-width ratio) of greater than 1 with a high probability of the cluster having damaged connective tissue. The ENC feature may refer to a circumference ratio of the equivalent ellipse of the scar which is defined as the ratio of the circumference of the ellipse to its diameter.

In an embodiment, the shape feature may be a universal descriptor feature for classification of many soft tissue lesions. A regular shape like round and oval may be associated with healthy tissue, while an irregular shape may be associated with damaged tissue. In an embodiment, the calcification feature may indicate whether there is calcification in the connective tissue layer. In an embodiment, this feature may be determined based on image intensity information of the ultrasound image (e.g., respective intensities of pixels of the image). For instance, a brighter pixel may indicate a higher likelihood of calcification at a location corresponding to the pixel. In some cases, the neural network may be trained to distinguish between intensity caused by calcification caused by calcification in the connective tissue layer versus calcification forming the underlying bone, and to ignore the effect of the bone when determining the calcification in the connective tissue layer. In some cases, the neural network may be configured to generate an updated ultrasound image that does not include an effect of calcium in the bone.

In an embodiment, the posterior shadow or posterior echo feature may reflect the characteristic of the posterior region of the tumor, where gray value is smaller than the region of the surrounding. In some cases, the echo characteristics feature may reflect a model of echo in the ultrasound image, including hypoechoic, isoechoic, hyperechoic, and complex echo. The echo signal of different tissues shows different characteristic in the ultrasound image. For example, muscle and fat have considerably higher water content than bone, and thus may have lower average image intensity. For example, muscle and fat in an ultrasound image may appear black. Bone generally has considerably less water content than muscle and fat, and may have higher average image intensity. For instance, the bone may appear as a white cluster in the ultrasound image.

In an embodiment, the slope feature may describe a 2D vector path (e.g., neutral, negative, or positive) of the Basement Membrane of the Hypodermis. Negative indicates an adhesion to the layer(s) below. Positive indicates an adhesion to the dermal layer. The contiguous feature may indicate whether the tissue represented by the ultrasound image has an organized, contiguous structure rather than a disorganized structure. For instance, healthy tissue may be organized and laminar in nature. Non-contiguous lines may be representative of adhesion to the dermal layer or calcification.

While the above discussion relates to assessing health of connective tissue and/or muscle tissue, the techniques discussed herein may be applied to ultrasound images represent other types of tissues or body parts.

Additional Discussion of Various Embodiments

Embodiment 1 relates to a computing system for processing ultrasound images, the computing system comprising: a communication interface configured to receive an ultrasound image that includes image data representing subdermal tissue; at least one processing circuit configured to: apply a trained neural network to the ultrasound image to generate at least one pliability parameter value which indicates pliability of the subdermal tissue, wherein the trained neural network has been trained with ultrasound images which have been defined as representing healthy subdermal tissue, and have been trained with ultrasound images which have been defined as representing damaged subdermal tissue; apply the trained neural network to the ultrasound image to generate an indication of whether any entrapped nerve is present in the subdermal tissue represented by the ultrasound image. The computing system further includes a display device configured to output the at least one pliability parameter value and the indication of whether any entrapped nerve is present in the subdermal tissue represented by the ultrasound image.

Embodiment 2 includes the computing system of embodiment 1, wherein the at least one processing circuit is further configured to apply the trained neural network to the ultrasound image to generate information which indicates one or more regions in the ultrasound image that represents damaged subdermal tissue.

Embodiment 3 includes the computing system of embodiment 2, wherein the trained neural network is trained to recognize, from the ultrasound image, clusters of tissue which are more dense than surrounding tissue and which lack a symmetric shape or a laminar structure, and wherein the one or more regions indicated by the information generated by the trained neural network represent at least one cluster of subdermal tissue which is more dense than surrounding subdermal tissue in the ultrasound image and which lacks a symmetric shape or a laminar structure.

Embodiment 4 includes the computing system of embodiment 3, wherein the trained neural network is trained to recognize clusters that lack laminar structure by recognizing a lack of distinct layers of different densities the ultrasound image representing the subdermal tissue, or by recognizing non-contiguous lines in the ultrasound image.

Embodiment 5 includes the computing system of any one of embodiments 1-4, wherein the subdermal tissue represented in the ultrasound image includes connective tissue and muscle tissue, and wherein the at least one pliability parameter value includes a first pliability parameter value indicating pliability of the connective tissue, and includes a second pliability parameter value indicating pliability of the muscle tissue.

Embodiment 6 includes the computing system of embodiment 5, wherein the at least one pliability parameter value includes a third pliability parameter value which indicates overall pliability of a combination of the connective tissue and the muscle tissue.

Embodiment 7 includes the computing system of any one of embodiments 1-6, wherein the trained neural network is trained with pliability scores that are based on a ratio of how much of subdermal tissue represented in ultrasound images is less dense than a defined density threshold and how much of the subdermal tissue is more dense than the defined density threshold.

Embodiment 8 includes the computing system of any one of embodiments 1-7, wherein the at least one processing circuit is configured to determine tissue density information which indicates how much of the subdermal tissue is less dense than a defined density threshold, and how much of the subdermal tissue is more dense than the defined density threshold.

Embodiment 9 includes the computing system of embodiment 8, wherein the at least one processing circuit is configured to determine the tissue density information by determining a tissue density value which indicates an overall density of a connective tissue layer of the subdermal tissue represented by the ultrasound image.

Embodiment 10 includes the computing system of embodiment 8 or 9, wherein the at least one processing circuit is configured to determine tissue density information by determining a spatial density value which indicates an amount of space occupied by the one or more regions representing damaged connective tissue within the connective tissue layer, wherein the method further comprises outputting the tissue density value and the spatial density value.

Embodiment 11 relates to method performed by the computing system of Embodiment 1.

Embodiment 12 relates to a computing system for processing ultrasound images, the computing system comprising: a communication interface configured to receive an ultrasound image that includes image data representing subdermal tissue; at least one processing circuit configured to apply a trained neural network to the ultrasound image to generate at least one pliability parameter value which indicates pliability of the subdermal tissue, wherein the trained neural network has been trained with ultrasound images which have been defined as representing healthy subdermal tissue, and have been trained with ultrasound images which have been defined as representing damaged subdermal tissue; and a display device configured to output the at least one pliability parameter value.

Embodiment 13 relates to a computing system for processing ultrasound images, the computing system comprising: receiving an ultrasound image that includes image data which represents subdermal tissue; identifying, based on a neural network, one or more regions of the ultrasound image that represent damaged connective tissue within a connective tissue layer located between a skin layer and a muscle layer of the subdermal tissue, wherein the one or more regions are identified by applying the image data as an input to the neural network, and wherein the neural network is trained with a training set of at least ultrasound images that represent damaged connective tissue and ultrasound images that represent healthy connective tissue; determining tissue density information that indicates density of the one or more regions identified by the neural network as representing damaged connective tissue; determining, based on the tissue density information, a parameter value or range of parameter values that indicates health of the connective tissue layer represented by the ultrasound image; and outputting, on a display device, the parameter value or range of parameter values that indicate health of the connective tissue layer.

Embodiment 14 relates to the method of embodiment 13, wherein the parameter value or range of parameter values is a pliability score which indicates stiffness or mobility of the connective tissue layer that is represented by the ultrasound image.

Embodiment 15 relates to the method of embodiment 14, wherein the tissue density information indicates how much of the connective tissue layer is less dense than a defined density threshold, and how much of the connective tissue layer is more dense than the defined density threshold, and wherein the pliability score is based on a ratio of how much of the connective tissue layer is less dense than the defined density threshold and how much of the connective tissue layer is more dense than the defined density threshold.

Embodiment 16 relates to the method of any one of embodiments 13-15, wherein determining the tissue density information includes determining a tissue density value which indicates an overall density of the connective tissue layer represented by the ultrasound image.

Embodiment 17 relates to the method of embodiment 16, wherein determining the tissue density information includes determining a spatial density value which indicates an amount of space occupied by the one or more regions representing damaged connective tissue within the connective tissue layer, wherein the method further comprises outputting the tissue density value and the spatial density value.

Embodiment 18 relates to the method of any one of embodiments 13-17, wherein the image data of the ultrasound image is based on ultrasound sensor data which sensed the connective tissue layer and at least a bone adjacent to the connective tissue layer, wherein the neural network is trained to distinguish between the bone and the connective tissue layer in the ultrasound image, and to recognize the one or more regions which represent damaged connective tissue from only the connective tissue layer and not from the bone.

Embodiment 19 relates to the method of embodiment 18, wherein the neural network is trained to recognize, from the ultrasound image, a plurality of features of the connective tissue layer, wherein the one or more regions that represent damaged connective tissue are identified based on the plurality of features, wherein the plurality of features include two or more of: (i) a cluster of tissue in the connective tissue layer having a density higher than a defined threshold, (ii) a cluster of tissue in the connective tissue layer having a shape that is not symmetric and is not round, (iii) a cluster of tissue in the connective tissue layer lacking laminar structure, or (iv) a cluster of tissue in the connective tissue layer having a blocked fluid channel.

Embodiment 20 relates to the method of embodiment 19, wherein the neural network is trained to recognize the cluster lacking laminar structure by recognizing a lack of distinct layers of different densities in the cluster, or by recognizing non-contiguous lines in the ultrasound image.

Embodiment 21 relates to the method of any one of embodiments 13-20, further comprising determining: based on the one or more regions that are identified by the neural network as representing damaged connective tissue within the connective tissue layer, an irregularity count which indicates how many regions within the connective tissue layer are damaged, wherein the method further comprises outputting the irregularity count on the display device.

Embodiment 22 relates to the method of embodiment any one of embodiments 13-21, further comprising identifying, based on the neural network, an additional set of one or more regions of the ultrasound image representing one or more locations within the connective tissue layer having an entrapped nerve, wherein the neural network is trained with information indicating nerve location within connective tissue layers, with information indicating whether patients associated with the connective tissue layers were experiencing pain, and with pain location for the patients.

Embodiment 23 relates to a method for evaluating connective tissue, the method comprising: receiving an ultrasound image that represents subdermal tissue; identifying, based on a neural network, one or more regions of the ultrasound image that represent one or more spaces within the connective tissue layer in which one or more nerves are entrapped, and wherein the neural network was trained with a training set of ultrasound images and with information that indicated nerve location within the ultrasound images; generating an updated ultrasound image by modifying the ultrasound image to add visual identifiers of the one or more regions; outputting the updated ultrasound image on a display device.

Embodiment 24 relates to a method for evaluating connective tissue, the method comprising: receiving a first ultrasound image that includes image data which represents a connective tissue layer, muscle, and a bone; generating, based on a neural network, a second ultrasound image that represents the connective tissue layer, or represents the connective tissue layer and the muscle, and that does not represent the bone, wherein the second ultrasound image is generated by applying the image data of the first ultrasound image as an input to the neural network, and wherein the neural network is trained to distinguish between the bone and the connective tissue layer in the first ultrasound image; determining, based on the second ultrasound image, a parameter value or range of parameter values that indicates health of the connective tissue layer represented by the second ultrasound image; and outputting, on a display device, the parameter value or range of parameter values that indicate health of the connective tissue layer.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A computing system for processing ultrasound images, the computing system comprising:
   a communication interface configured to receive an ultrasound image that includes image data representing subdermal tissue;
   at least one processing circuit configured to:
      apply a trained neural network to the ultrasound image to generate at least one pliability parameter value which indicates pliability of the subdermal tissue, wherein the trained neural network has been trained with ultrasound images which have been defined as representing healthy subdermal tissue, and have been trained with ultrasound images which have been defined as representing damaged subdermal tissue;
      apply the trained neural network to the ultrasound image to generate an indication of whether any entrapped nerve is present in the subdermal tissue represented by the ultrasound image; and
   a display device configured to output the at least one pliability parameter value and the indication of whether any entrapped nerve is present in the subdermal tissue represented by the ultrasound image.

2. The computing system of claim 1, wherein the at least one processing circuit is further configured to apply the trained neural network to the ultrasound image to generate information which indicates one or more regions in the ultrasound image that represents damaged subdermal tissue.

3. The computing system of claim 2, wherein the trained neural network is trained to recognize, from the ultrasound image, clusters of tissue which are more dense than surrounding tissue and which lack a symmetric shape or a laminar structure, and wherein the one or more regions indicated by the information generated by the trained neural network represent at least one cluster of subdermal tissue which is more dense than surrounding subdermal tissue in the ultrasound image and which lacks a symmetric shape or a laminar structure.

4. The computing system of claim 3, wherein the trained neural network is trained to recognize clusters that lack laminar structure by recognizing a lack of distinct layers of different densities the ultrasound image representing the subdermal tissue, or by recognizing non-contiguous lines in the ultrasound image.

5. The computing system of claim 2, wherein the subdermal tissue represented in the ultrasound image includes connective tissue and muscle tissue, and wherein the at least one pliability parameter value includes a first pliability parameter value indicating pliability of the connective tissue, and includes a second pliability parameter value indicating pliability of the muscle tissue.

6. The computing system of claim 5, wherein the at least one pliability parameter value includes a third pliability parameter value which indicates overall pliability of a combination of the connective tissue and the muscle tissue.

7. The computing system of claim 1, wherein the trained neural network is trained with pliability scores that are based on a ratio of how much of subdermal tissue represented in ultrasound images is less dense than a defined density threshold and how much of the subdermal tissue is more dense than the defined density threshold.

8. The computing system of claim 1, wherein the at least one processing circuit is configured to determine tissue density information which indicates how much of the subdermal tissue is less dense than a defined density threshold, and how much of the subdermal tissue is more dense than the defined density threshold.

9. The computing system of claim 8, wherein the at least one processing circuit is configured to determine the tissue density information by determining a tissue density value which indicates an overall density of a connective tissue layer of the subdermal tissue represented by the ultrasound image.

10. The computing system of claim 8, wherein the at least one processing circuit is configured to determine tissue density information by determining a spatial density value which indicates an amount of space occupied by the one or more regions representing damaged connective tissue within the connective tissue layer, wherein the method further comprises outputting the tissue density value and the spatial density value.

11. A method performed by a computing system, the method comprising:
- receiving an ultrasound image that includes image data representing subdermal tissue;
- apply a trained neural network to the ultrasound image to generate at least one pliability parameter value which indicates pliability of the subdermal tissue, wherein the trained neural network has been trained with ultrasound images which have been defined as representing healthy subdermal tissue, and have been trained with ultrasound images which have been defined as representing damaged subdermal tissue;
- apply the trained neural network to the ultrasound image to generate an indication of whether any entrapped nerve is present in the subdermal tissue represented by the ultrasound image; and
- displaying the at least one pliability parameter value and the indication of whether any entrapped nerve is present in the subdermal tissue represented by the ultrasound image.

12. A computing system for processing ultrasound images, the computing system comprising:
- a communication interface configured to receive an ultrasound image that includes image data representing subdermal tissue;
- at least one processing circuit configured to apply a trained neural network to the ultrasound image to generate at least one pliability parameter value which indicates pliability of the subdermal tissue, wherein the trained neural network has been trained with ultrasound images which have been defined as representing healthy subdermal tissue, and have been trained with ultrasound images which have been defined as representing damaged subdermal tissue; and
- a display device configured to output the at least one pliability parameter value.

* * * * *